United States Patent
Zhu et al.

(10) Patent No.: US 6,425,901 B1
(45) Date of Patent: *Jul. 30, 2002

(54) VASCULAR WOUND CLOSURE SYSTEM

(75) Inventors: Yong Hua Zhu, Loma Linda; Wolff M. Kirsch, Redlands, both of CA (US)

(73) Assignee: Loma Linda University Medical Center, Loma Linda, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/984,757

(22) Filed: Dec. 4, 1997

Related U.S. Application Data

(63) Continuation-in-part of application No. 08/943,369, filed on Oct. 3, 1997, now abandoned, which is a continuation-in-part of application No. 08/764,611, filed on Dec. 5, 1996, now Pat. No. 6,004,341.
(60) Provisional application No. 60/009,643, filed on Dec. 7, 1995.

(51) Int. Cl.$^7$ .............................................. A61B 17/10
(52) U.S. Cl. ........................ 606/142; 606/208; 600/208; 600/219
(58) Field of Search ................................ 606/205, 207, 606/209, 213, 142–143, 208, 51, 52; 600/208, 222, 225, 219, 210, 215; 433/159; 81/321, 316, 318, 322, 323, 326, 328

(56) References Cited

U.S. PATENT DOCUMENTS

| | | | |
|---|---|---|---|
| 1,064,307 A | 6/1913 | Fleming |
| 3,518,993 A | 7/1970 | Blake |
| 3,653,388 A | 4/1972 | Tenckhoff |
| 3,774,438 A | 11/1973 | Weston |

(List continued on next page.)

FOREIGN PATENT DOCUMENTS

| | | |
|---|---|---|
| DE | 9202738 | 9/1992 |
| EP | 0493810 | 7/1992 |
| EP | 0646350 | 4/1995 |
| GB | 2142244 | 1/1985 |
| WO | 9624291 | 8/1996 |
| WO | 9720505 | 6/1997 |

*Primary Examiner*—Cary E. O'Connor
(74) *Attorney, Agent, or Firm*—Knobbe, Martens, Olson & Bear, LLP

(57) ABSTRACT

A system which facilitates the closure of puncture wounds in the vasculature of a patient by helping locate and isolate the site of the puncture wound in the patient. A tube or catheter having an indicator hole for aspirating blood assists in locating the exact site of the wound. A retractor moves the surrounding tissue laterally forming an access path to the wound, and acts as a guide for the wound closure device. The retractor and accessories are preferably used in combination with a surgical clip applicator which delivers clips to the site of the wound, but can also be used with other methods of wound closure such as suturing and stapling.

27 Claims, 13 Drawing Sheets

U.S. PATENT DOCUMENTS

| | | |
|---|---|---|
| 4,064,881 A | 12/1977 | Meredith |
| 4,166,466 A | 9/1979 | Jarvik |
| 4,325,376 A | 4/1982 | Klieman et al. |
| 4,351,466 A | 9/1982 | Noiles |
| 4,440,170 A | 4/1984 | Golden et al. |
| 4,487,204 A | 12/1984 | Hrouda |
| 4,492,232 A | 1/1985 | Green |
| 4,523,592 A | 6/1985 | Daniel |
| 4,530,698 A | 7/1985 | Goldstein et al |
| 4,534,351 A | 8/1985 | Rothfuss et al. |
| 4,539,990 A | 9/1985 | Stivala |
| 4,593,693 A | 6/1986 | Schenck |
| 4,611,595 A | 9/1986 | Klieman |
| 4,616,650 A | 10/1986 | Green et al. |
| 4,622,970 A | 11/1986 | Wozniak |
| 4,651,733 A | 3/1987 | Mobin-Uddin |
| 4,693,249 A | 9/1987 | Schenck et al. |
| 4,889,112 A * | 12/1989 | Schachner et al. .......... 606/108 |
| 4,917,087 A | 4/1990 | Walsh et al. |
| 4,930,674 A | 6/1990 | Barak |
| 4,931,059 A | 6/1990 | Cooper |
| 4,934,364 A | 6/1990 | Green |
| 4,984,564 A | 1/1991 | Yuen |
| 5,015,249 A | 5/1991 | Nakato et al. |
| 5,147,381 A | 9/1992 | Heimerl et al |
| 5,207,229 A | 5/1993 | Winters |
| 5,297,714 A | 3/1994 | Kramer |
| 5,300,065 A | 4/1994 | Anderson |
| 5,342,373 A | 8/1994 | Stefanchik et al. |
| 5,360,397 A | 11/1994 | Pinchuk |
| 5,380,338 A * | 1/1995 | Christian .................... 606/130 |
| 5,383,881 A | 1/1995 | Green et al. |
| 5,580,344 A | 12/1996 | Hasson |
| 5,591,203 A * | 1/1997 | Fahy ......................... 606/207 |
| 5,613,948 A | 3/1997 | Avellanet |
| 5,624,454 A * | 4/1997 | Palti et al. ................... 606/151 |
| 5,653,729 A * | 8/1997 | Chappuis et al. ........... 606/207 |
| 5,674,231 A | 10/1997 | Green et al. |
| 5,697,933 A * | 12/1997 | Gundlapalli et al. .......... 606/96 |
| 5,746,757 A * | 5/1998 | McGuire .................... 606/148 |
| 5,797,919 A * | 8/1998 | Brinson ..................... 606/105 |
| 5,910,155 A * | 6/1999 | Ratcliff et al. .............. 606/213 |

* cited by examiner

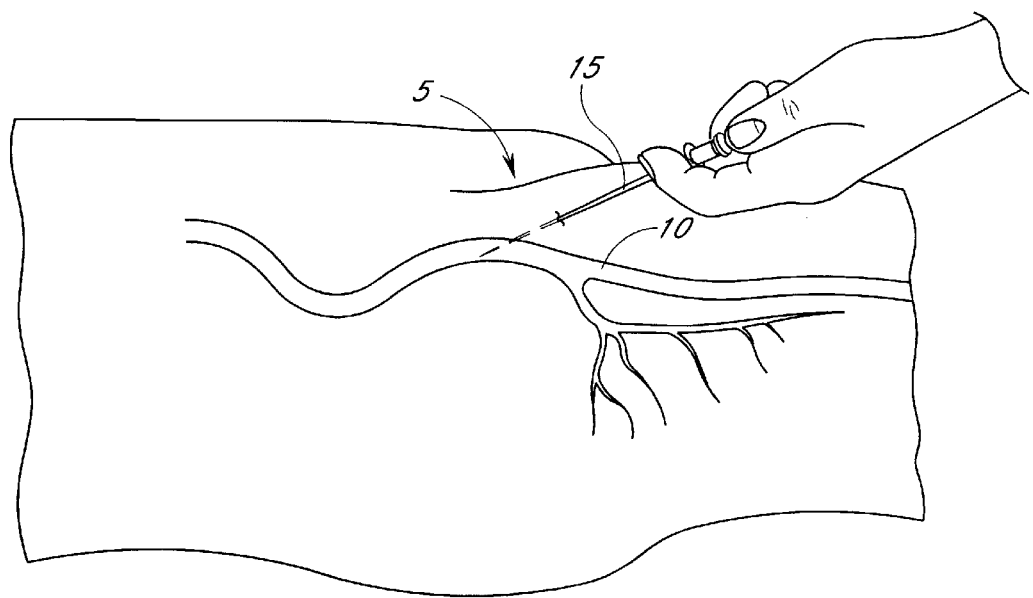
Fig.1
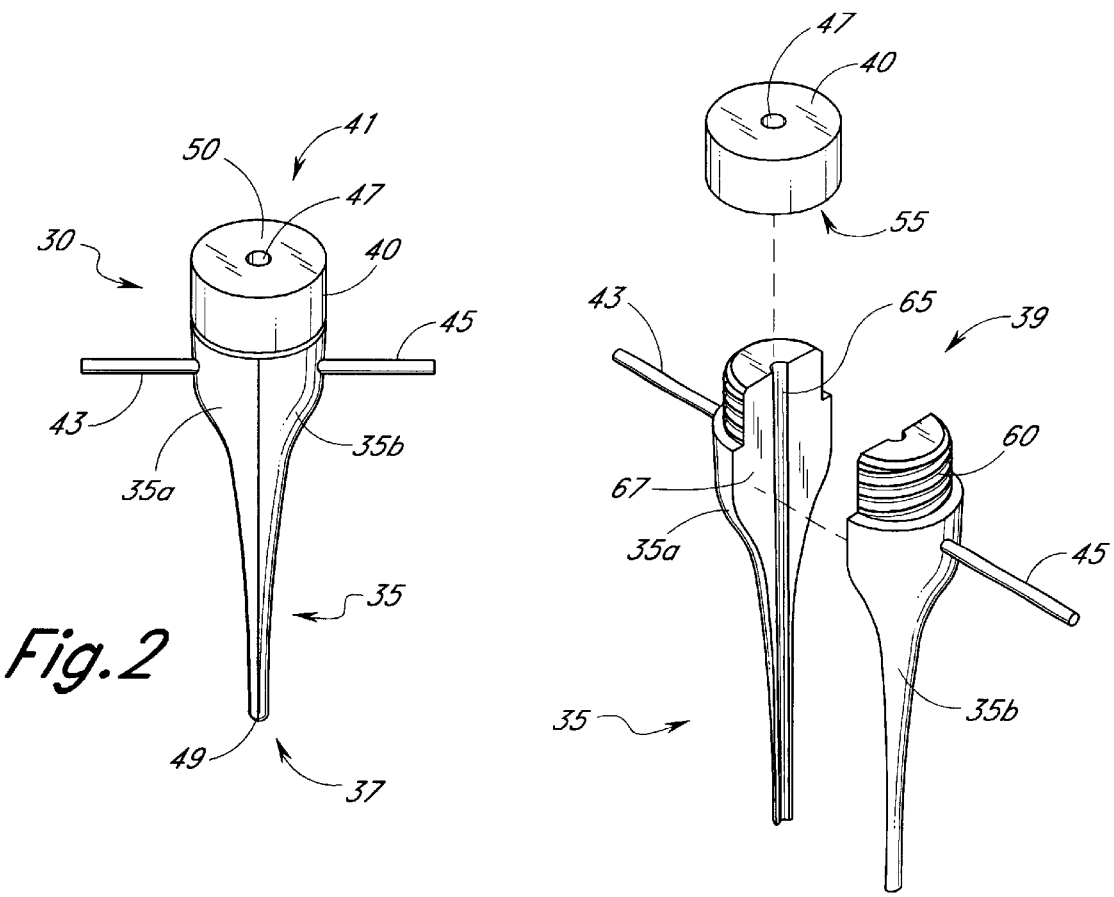
Fig.2
Fig.3

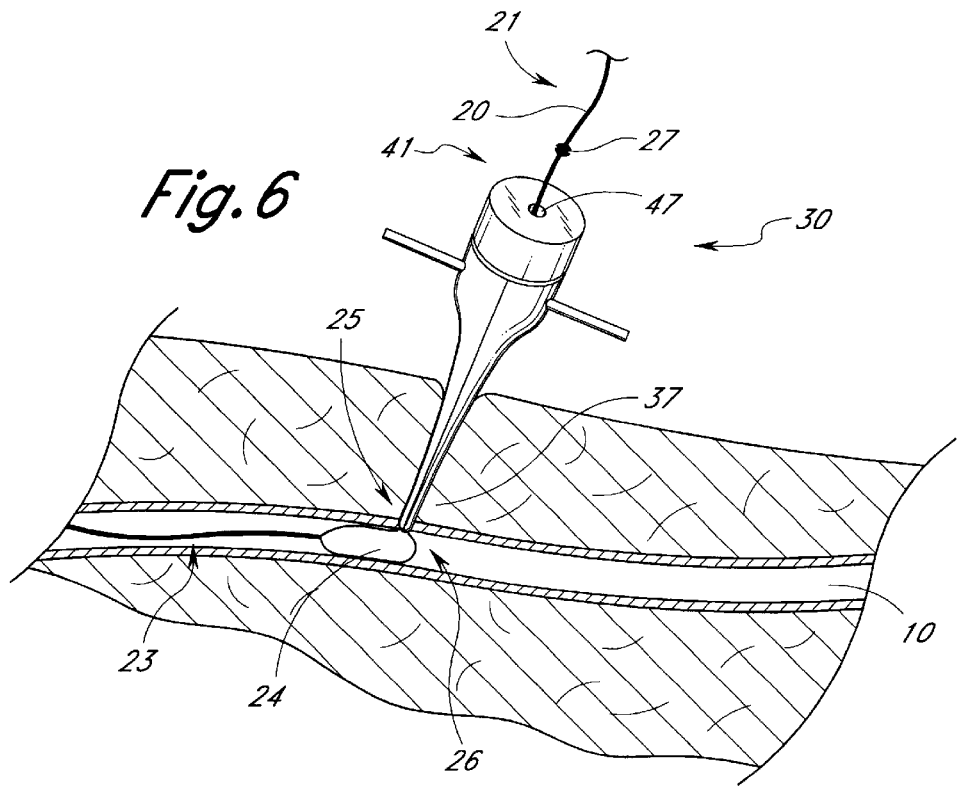
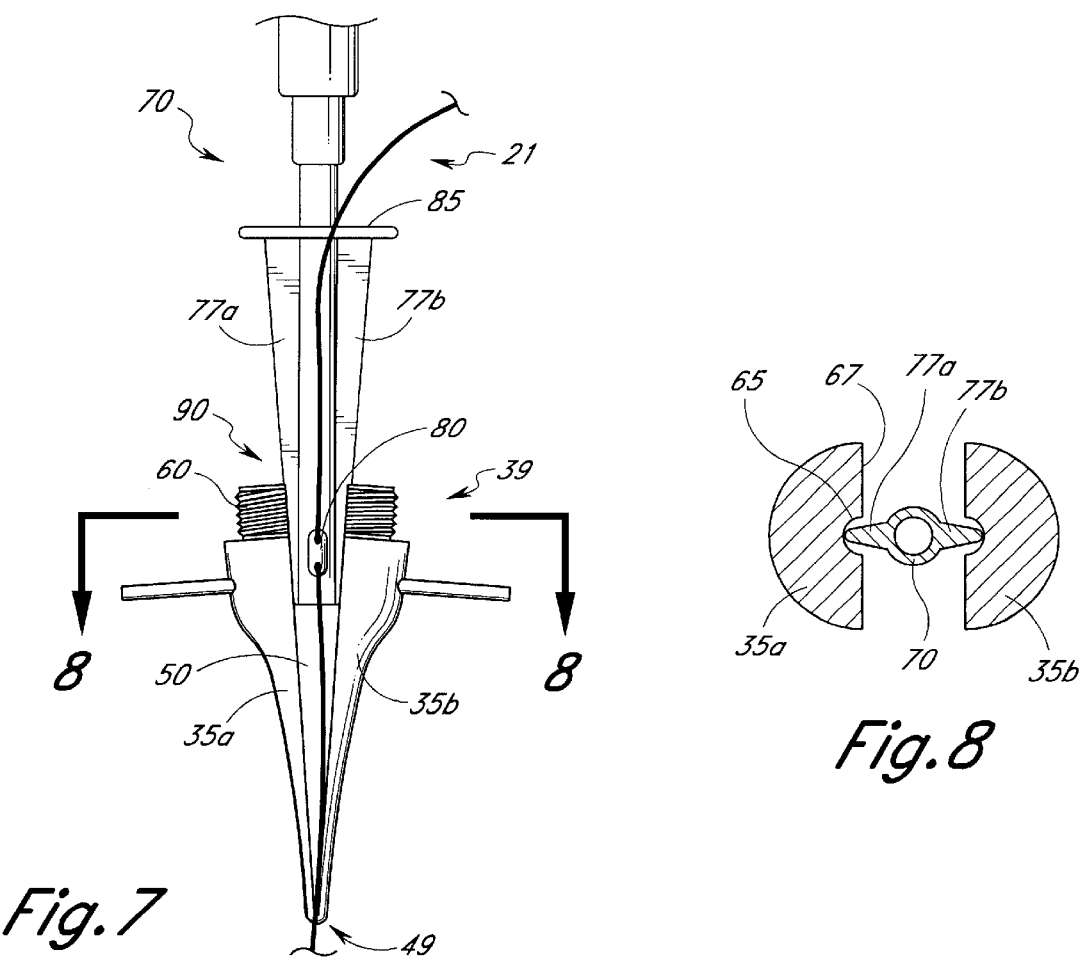

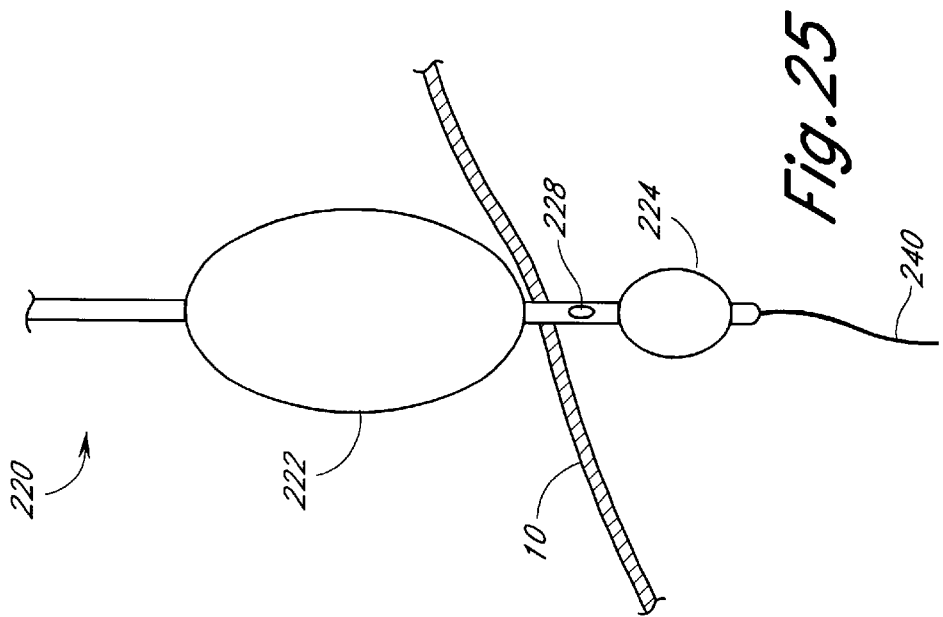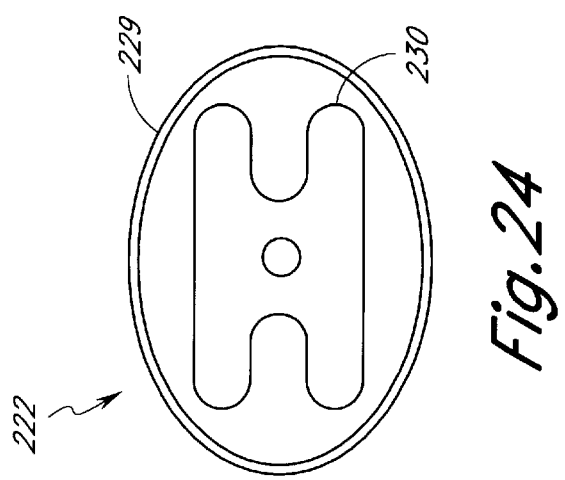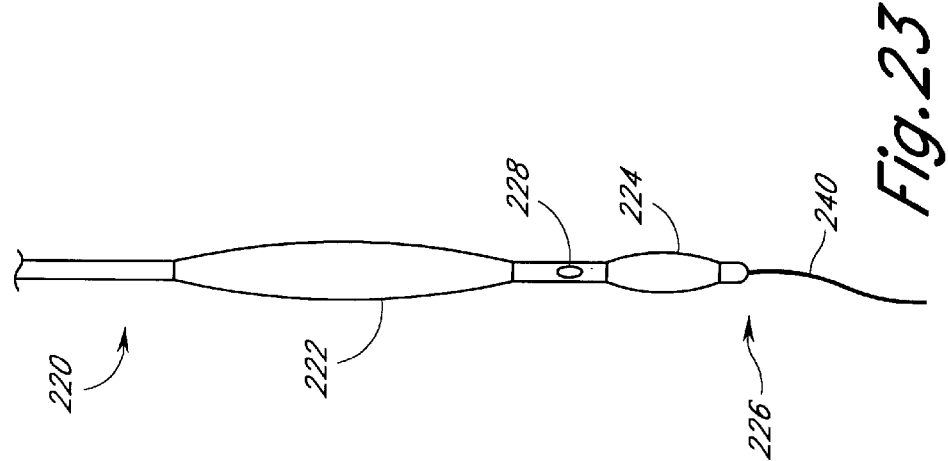

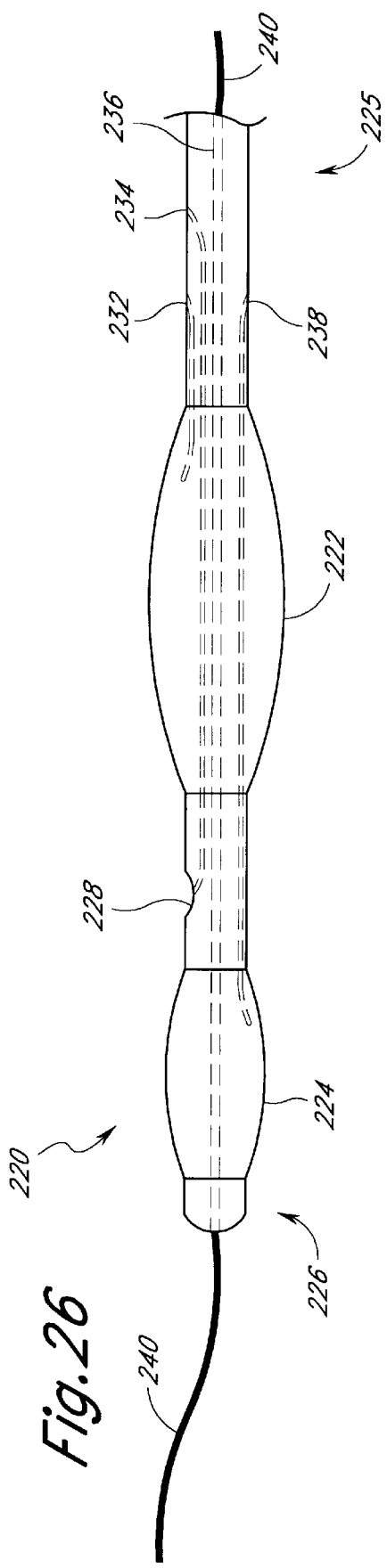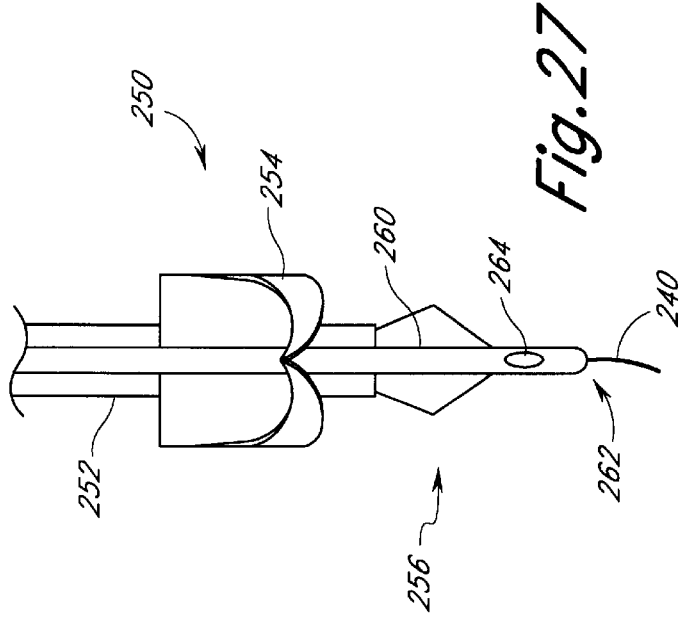

VASCULAR WOUND CLOSURE SYSTEM

CROSS-REFERENCE TO RELATED APPLICATIONS

This application is a continuation-in-part of U.S. application Ser. No. 08/943,369, filed Oct. 3, 1997, now abandoned, which is a continuation-in-part of U.S. application Ser. No. 08/764,611, filed Dec. 5, 1996, now U.S. Pat. No. 6,004,341, which claims the benefit of U.S. Provisional Application Ser. No. 60/009,643 filed Dec. 7, 1995.

FIELD OF THE INVENTION

The present invention relates to a system which assists in the closure of puncture or other wounds in the vasculature of a patient. Specifically, the invention relates to devices which aid in locating and isolating the wound in the vasculature and guiding an appropriate wound closure device to the site, so that the wound may be closed using surgical clips, sutures, or staples.

BACKGROUND OF THE INVENTION

Transluminal balloon angioplasty is used in the treatment of peripheral vascular disease to increase or restore blood flow through a significantly narrowed artery in a limb; it is also used in the treatment of blockage of the coronary arteries. In fact, coronary angioplasty has emerged as a major viable alternative to bypass surgery for revascularization of stenotic and occluded coronary arteries. Unlike bypass surgery, angioplasty does not require general anesthesia, opening of the chest wall, use of a heart-lung machine, or transfusion of blood. Angioplasty is not only less invasive and less traumatic to the patient, it is also less expensive because of the shorter hospital stay and shorter recovery time.

Transluminal balloon angioplasty is performed by first inserting a hollow needle through the skin and into the patient's femoral artery. A guidewire is advanced through the hollow needle and into the artery, then along the patient's vasculature toward the site of the blocked blood vessel or heart valve to be treated. X-ray imaging is used to help move the guidewire through the vascular system and into position just past the stenosis to be treated. A balloon catheter is then threaded over the guidewire and advanced until the deflated balloon is within the stenosis. The balloon is then repeatedly inflated to widen the narrowed blood vessel. After the procedure is complete, the catheter and guidewire are withdrawn from the blood vessels and the patient.

Angiography, which is used to detect diseases that alter the appearance of blood vessels, is performed in a similar manner. A hollow needle is first inserted through the skin and into the femoral artery, and a guidewire is then inserted through the needle and into the affected blood vessel. A catheter is then threaded over the guidewire and into the blood vessel to be examined, using x-ray imaging to guide the catheter to the desired position. Contrast medium is then injected, and a rapid sequence of x-ray pictures are taken so that blood flow along the affected vessel can be studied. Once complete, the catheter and guidewire are removed from the patient's body.

After the catheter and guidewire used during angioplasty or angiography are removed, the puncture wound in the femoral artery must be closed and the bleeding through the puncture site in the artery stopped. Currently, ice packs and/or pressure are applied to the artery for a period lasting up to several hours in an attempt to stop the bleeding. There exists, however, a significant chance that upon movement by the patient, the wound will reopen and begin bleeding again. Although efforts have been made to close the puncture wound using staples, clips, and sutures, they have been unsuccessful, largely due to the inability to clearly locate and visualize the puncture wound in the femoral artery.

Other wounds in the vasculature of a patient can also be difficult to locate and access. Thus, a device and method to facilitate the closure wounds in the vasculature of a patient, such as femoral artery puncture wounds following transluminal balloon angioplasty and angiography, would be extremely beneficial. A device having the ability to aid in locating the puncture wound and facilitating the closure of the wound using staples, clips, or sutures would eliminate the prolonged bleeding currently associated with such wounds.

SUMMARY OF THE INVENTION

The wound closure system of the present invention aids in locating and isolating a puncture wound in the vasculature of a patient. The system can be used in conjunction with a guidewire which is normally inserted into the vasculature during diagnostic and therapeutic procedures. The devices of the present invention aid the physician in closing the wound, thus eliminating prolonged bleeding associated with these procedures.

In accordance with one aspect of the present invention, there is provided a device to facilitate the closure of wounds in the femoral artery. This retractor comprises a body portion separable into two halves, each of the halves having a flat internal surface with a groove, such that when the internal surfaces abut one another, the grooves form a channel through the entire length of the body portion. The retractor has a collar portion at one end, having at least one guide passage which traverses both halves of the body portion, and at least one pin which is insertable into the guide passage. A handle extends laterally from the pin to allow the user to easily manipulate the device. At least one set screw hole can be provided in the collar portion at a right angle to the guide passage, and at least one set screw inserted into the set screw hole to secure the device to the pins.

The device can be made of a biocompatible engineering polymer, such as polypropylene, polyethylene, or polyterephthalate. Alternatively, an elastomer or a metal can be used to make the device.

A hollow dilator adapted to receive a guidewire is preferably used in conjunction with the retractor. The dilator is inserted through the channel in the body portion of the retractor, and extends past the distal end of the reactor. The dilator preferably includes at least one indicator hole located at the distal end, which extends past the end of the retractor. The dilator has a double-sleeved inflatable balloon mounted on its distal end just proximal to the indicator hole, and a second inflatable balloon mounted just distal to the indicator hole. These balloons help anchor the dilator in place, and provide access to the puncture wound from the surface of the patient's body. A guidewire is used to help guide the insertion of the dilator. The guidewire is inserted through the hollow dilator, and the dilator advanced over the guidewire into its proper position.

Another aspect of the present invention includes a system for facilitating the closure of wounds in the vasculature of a patient. The system includes a retractor as described above, a hollow dilator adapted to receive a guidewire, and a guidewire. The guidewire is inserted through the dilator, and the dilator is inserted through the channel in the retractor.

Preferably, a guide assembly adapted to be reversibly attached to a surgical clip applicator is used. The guide assembly receives the guidewire to help guide the clip applicator to the site of the puncture wound.

The dilator preferably has a source of negative pressure connected to its proximal end in fluid communication with the hollow dilator. The source of negative pressure can be a syringe or any other appropriate source.

A method for facilitating the closure of a wound in the vasculature of a patient is also described. A guidewire is first inserted into the patient's vasculature through the wound, until the distal end of the guidewire is within the vasculature and the proximal end remains outside the patient's body. The proximal end of the guidewire is inserted into the distal end of a hollow dilator having a double-sleeved balloon and a second balloon distal the double-sleeved balloon mounted on it. The dilator is advanced over the guidewire until it reaches the wound. The balloons are inflated to anchor the dilator in position, and the proximal end of the dilator is inserted into the distal end of a retractor. The retractor is advanced between the two sleeves of the double-sleeved balloon. The two halves of the retractor are separated and the dilator and the inner sleeve of the double-sleeved balloon are removed from the patient. Using the retractor and the outer sleeve of the balloon as a guide, the wound is accessed and closed by means such as clipping, stapling, or suturing.

Preferably, a source of negative pressure is provided on the proximal end of the dilator during insertion, until blood is drawn into the dilator from the vasculature. This assists the user in determining when the dilator is properly positioned.

A hollow indicator tube mounted on a surgical clip applicator is preferably used to close the wound. The applicator is advanced over the guidewire and through the channel in the retractor until the applicator contacts the wound. To aid proper insertion, a source of negative pressure is provided at the proximal end of the indicator tube, until blood is drawn into the indicator tube from the vasculature.

In yet another embodiment of the retractor used to facilitate wound closure, the retractor has a body portion and a handle portion. At its distal end, the body portion has a retracting portion having two movable halves which extend away from the body portion. The halves are formed such that when the internal surfaces abut one another, a channel is formed which extends completely through the retracting portion. The handle portion connects to the body portion and controls the movement of the two moveable halves. Preferably, the handle portion comprises two handles, and a loop extending from one handle to the other. This loop surrounds a screw mounted on the other handle. This locking mechanism acts to secure the position of the handles and the retracting portion of the retractor.

A hollow catheter having an open proximal end and an open distal end, adapted to receive a guidewire therethrough, is used in conjunction with the retractor. The hollow catheter is inserted through the channel in the retracting portion of the retractor. The catheter is preferably a dual-lumen catheter, having an inner lumen adapted to receive a guidewire, and an outer lumen which surrounds the inner lumen. The outer lumen has at least one indicator hole located in an outer wall to allow for the aspiration of blood through the outer lumen. This helps position the catheter properly within the patient's body.

The retractor and dual-lumen catheter are used in the following manner. The retractor is mounted on the outside of the distal end of the catheter, approximately 0.5 mm behind the indicator hole located in the outside wall of the catheter. The proximal end of a guidewire which is already in place in the patient as a result of a diagnostic or therapeutic procedure, is inserted into the distal end of the inner lumen of the dual-lumen catheter, and the catheter and retractor are advanced as a single unit over the guidewire.

Preferably, a source of negative pressure is provided at the proximal end of the outer lumen of the dual-lumen catheter during its advancement. As soon as blood is drawn into the outer lumen through the indicator hole, advancement of the catheter and retractor are stopped. The two halves of the retracting portion are then separated to expose the wound, the catheter and guidewire are removed, and the wound is closed.

Further, a second catheter having an inflatable balloon on its distal end may be used. Once the retractor and double-lumen catheter are in place, the guidewire is removed from the patient through the inner lumen of the dual-lumen catheter. The inner catheter having an inflatable balloon mounted on its distal end is inserted through the inner lumen of the dual-lumen catheter and into the patient. Once inside the vasculature, the balloon is inflated and drawn in a proximal direction until resistance is felt. This helps to anchor the catheter in place as well as stop the bleeding during the closing of the wound. The dual-lumen catheter is removed, and the inner catheter is used to guide a closing device to the wound. The wound is closed as the balloon is deflated and the inner catheter is removed. Finally, the retractor is removed.

The present invention advantageously provides a simple and safe method of facilitating the closure of a wound in the vasculature of a patient, and the devices which facilitate this method. A retractor, used in conjunction with a guidewire, dilator or catheter, helps locate and isolate the site of the puncture wound in the patient. The retractor moves the surrounding tissue laterally as it is advanced into the patient, and acts as a guide for the physician in locating the exact site of the wound. The retractor is preferably used in combination with a surgical clip applicator which delivers clips to the site of the wound, but can also be used with other methods of wound closure such as suturing and stapling. The present invention eliminates the prolonged bleeding associated with current cardiac diagnostic and therapeutic procedures, and provides a significant advancement in the medical field.

BRIEF DESCRIPTION OF THE DRAWINGS

FIG. 1 is a side view of a portion of a human body, showing the site where the femoral artery is typically accessed and punctured during angioplasty or angiography.

FIG. 2 is a perspective view of one embodiment of the wound closure device of the present invention.

FIG. 3 is an exploded perspective view of the wound closure device of the present invention.

FIG. 6 is a partial cross-sectional view of a portion of a human body, showing the femoral artery having a guidewire positioned therein, and a perspective view of the retractor of the present invention positioned over the guidewire, with its distal tip at the site of the puncture in the femoral artery.

FIG. 7 is a side view of the retractor with its cap removed and the wings of the surgical clip applicator inserted into the grooves within the retractor.

FIG. 8 is a cross-sectional view of the clip applicator and retractor taken along line 8—8 in FIG. 7.

FIG. 23 is a perspective view of an alternate embodiment of a dilator having a double-sleeved balloon and a distal balloon mounted thereon in accordance with the present invention.

FIG. 24 is a top view of another embodiment of the double-sleeved balloon, illustrating the I-shaped inner sleeve.

FIG. 25 is a perspective view of the alternate embodiment of the dilator of FIG. 23, showing the balloons inflated.

FIG. 26 is a cross-sectional view of the dilator of the present invention, illustrating the various lumens in the dilator.

FIG. 27 is a side view of the distal end of a surgical clip applicator with an indicator tube mounted thereon.

DETAILED DESCRIPTION OF THE PREFERRED EMBODIMENT

Introduction

Although the description which follows details the closure of a puncture wound in a femoral artery, the present invention is not intended to be limited to use only with the femoral artery. Rather, the description which follows is exemplary only, and those of skill in the art can readily modify the method described below to use with other types of wounds to the vascular system.

Figure 4:
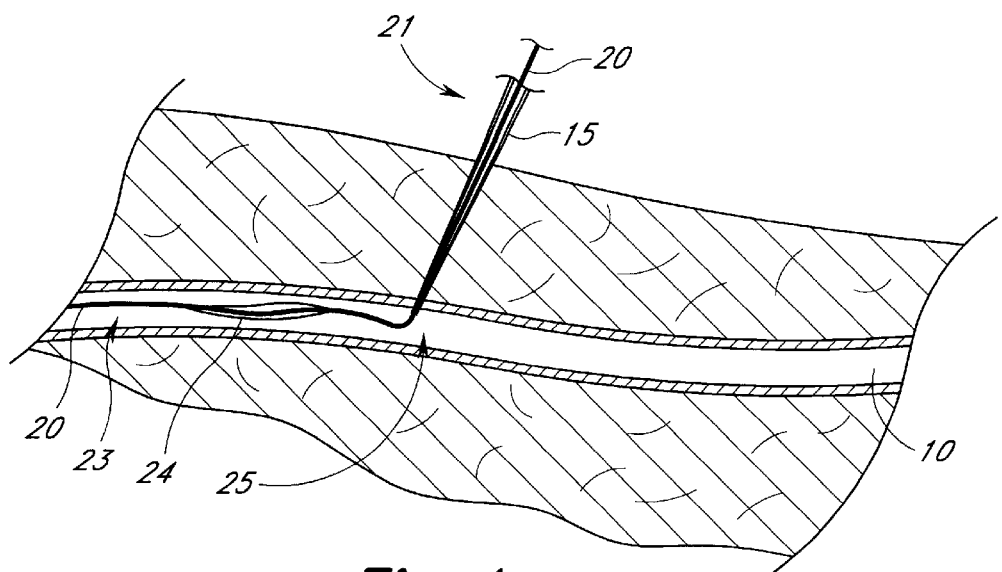
FIG. 4 is a cross-sectional view of a portion of a human body, showing the femoral artery accessed via a hollow needle, and a guidewire having an inflatable balloon attached, inserted through the hollow needle and into the femoral artery.

Referring first to FIG. 1, there is shown a side view of a portion of a human body, showing a site 5 where a femoral artery 10 is typically accessed and punctured during angioplasty or angiography. During these procedures, a hollow needle 15 is first inserted through the skin and into the femoral artery 10. A guidewire 20 is then inserted through the proximal end of the hollow needle 15 and into the artery 10, as illustrated in FIG. 4, and the needle 15 is withdrawn from the patient. The guidewire 20 is advanced through the patient's vasculature, often using x-ray imaging as an aid in directing the guidewire 20 to the desired location.

Once the guidewire 20 is in the desired location, a catheter is used. The proximal end of the guidewire 21 is inserted into the distal end of the catheter, and the catheter is threaded over the guidewire 20 and advanced to the desired location. In the case of angioplasty, the catheter has an inflatable balloon attached at its distal end. Once in position within the stenosis, the balloon is repeatedly inflated and deflated to widen the narrowed blood vessel. In the case of angiography, a catheter is threaded over the guidewire 20 as just described and into the blood vessel to be examined. Contrast medium is then injected, and a rapid sequence of x-ray pictures are taken so that blood flow along the affected vessel can be studied.

After either of these procedures is completed, the catheter and guidewire 20 are withdrawn from the blood vessel and the patient. The puncture wound 25 in the femoral artery 10 caused by the insertion of the hollow needle 15, guidewire 20 and catheter must be closed and the bleeding through the puncture site 25 in the artery 10 stopped.

Construction of the Retractor

In order to facilitate the closure of the wound 25 in the femoral artery 10, a retractor 30 is employed. The retractor 30, illustrated in FIGS. 2 and 3, comprises a body portion 35 and a cap 40. The body 35 of the retractor 30 has a narrow, tapered distal end 37, and a broader circular proximal end 41. The device 30 has two handles 43, 45 located on its body 35, one on each half 35a, 35b. The handles 43, 45 are positioned approximately one-third of the way from the proximal end of the retractor 41, and extend laterally from the body of the retractor 35. These handles 43, 45 assist the user in handling the device 30. The retractor 30 also comprises a circular cap 40 at its proximal end 41, having a hole 47 therethrough. This hole 47 extends into a channel 50 which runs the entire length of the device 30.

As illustrated in FIG. 3, the cap 40 and body 35 of the retractor 30 comprise three separable pieces: the cap portion 40 and the two halves of the body portion 35a, 35b. The removable cap 40 is internally threaded 55. The proximal end 39 of the two halves of the body 35a, 35b are externally threaded 60, and are adapted to removably receive the cap 40. Each half of the body of the retractor 35a, 35b has a semi-circular groove 65 on its flat internal surface 67. When the cap 40 is securely screwed onto the two halves of the body 35a, 35b as illustrated in FIG. 2, the three pieces are joined together, and the semi-circular grooves 65 form a channel 50 running through the interior of the device 30, which starts at the hole in the cap 47 at the proximal end 41 and continues through the body 35, ending at a small hole 49 in the distal end of the retractor 37 where the two halves of the body 35a, 35b come together. When the cap 40 is unscrewed from the body 35, the two halves of the body 35a, 35b may be moved apart from one another, as illustrated in FIG. 3.

Alternate Embodiment of the Retractor

Figure 9:
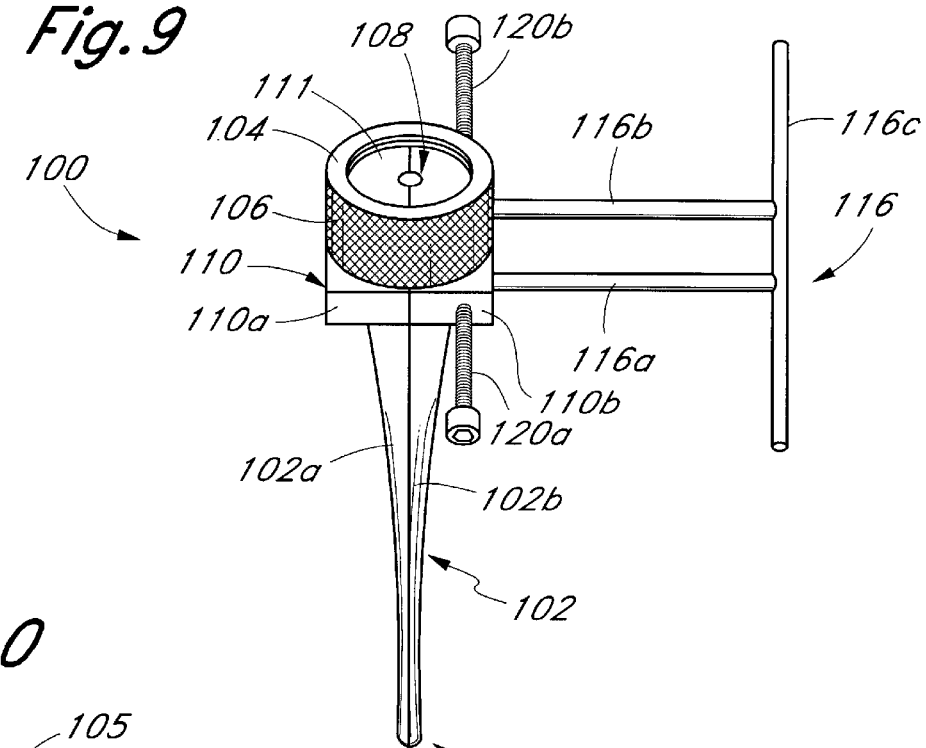
FIG. 9 is a perspective view of an alternate embodiment of a femoral artery closure device in accordance with the present invention.
Figure 10:
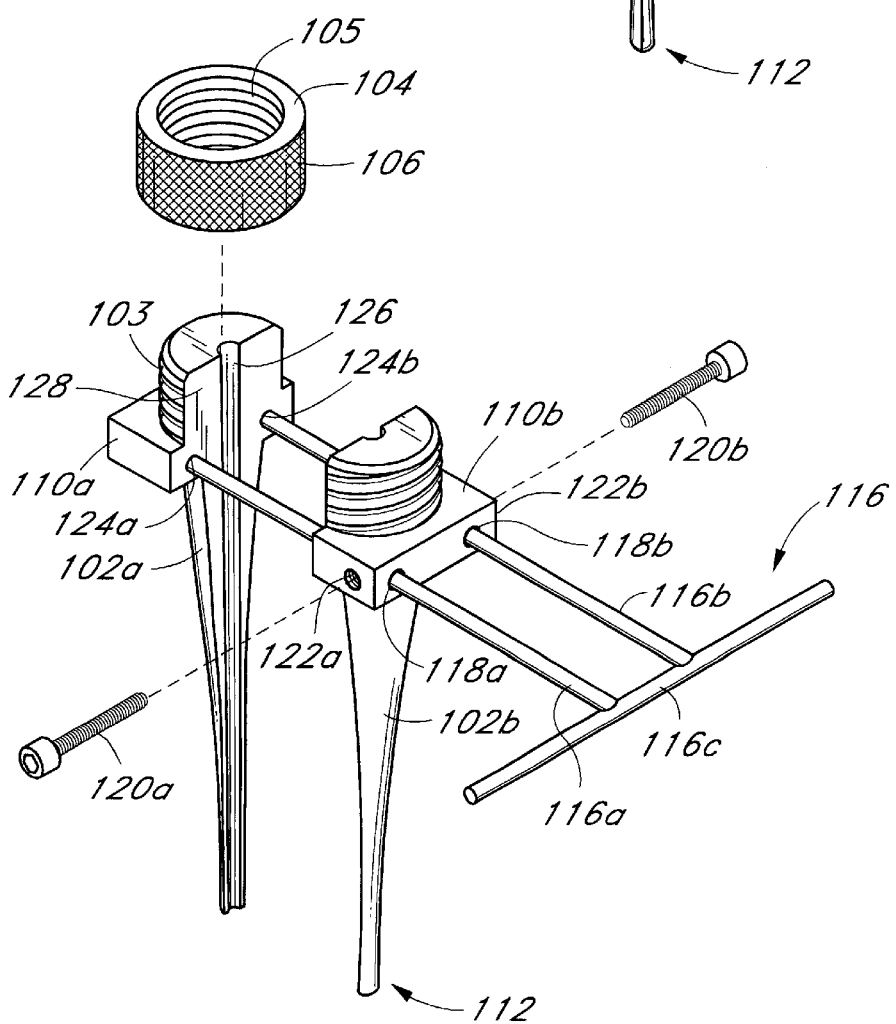
FIG. 10 is an exploded perspective view of the alternate embodiment of the femoral artery closure device illustrated in FIG. 9.

Another preferred embodiment of the invention is illustrated in FIGS. 9–10. In this embodiment, the retractor 100 includes a retraction mechanism whereby the two halves 102a, 102b of the retractor body 102 can be moved apart from one another a desired distance, while maintaining their alignment. The retractor again comprises a body portion 102, and an annular cap 104. The two halves 102a, 102b of the body are initially held together by the internally threaded 105 cap 104. This cap 104 is screwed on and off the externally threaded halves 102a, 102b of the retractor body. The outer surface of the cap 106 can be textured to ease hand tightening and loosening of the cap 106. As illustrated in FIG. 10, each half 102a, 102b of the retractor body again has a semicircular groove 126 running longitudinally down the center of its flat internal surface 128. When the cap 104 is securely screwed onto the two halves 102a, 102b of the retractor body, such that the internal surfaces 128 abut one another, the semicircular grooves 126 form a channel 108. The cap 104 is open on both ends and through its center to permit access to the channel 108.

The retractor 100, as illustrated in FIGS. 9–10, further comprises a collar 110 located on the retractor body 102 just distal to the externally threaded proximal end 103; a pin assembly 116, comprising two parallel pins 116a, 116b attached at one end to a perpendicular handle 116c; and two set screws 120a, 120b. As illustrated in FIG. 10, the pins 116a, 116b traverse guide passages 118a, 118b bored through the collar region 110b of one half 102b of the retractor body and are insertable within holes 124a, 124b in the collar region 110a of the other half 102a of the retractor body, such that one half 102b of the retractor body can slide apart from the other half 102a on the pins 116a, 116b. The collar 110b includes internally threaded holes 122a, 122b adapted to receive externally threaded set screws 120a, 120b. The set screw holes 122a, 122b enter the collar region 110a at right angles to the pin guide passages 118a, 118b, such that when the set screws 120a, 120b are advanced, they tighten upon the pins 116a, 116b and thus, fix the distance between the two halves 102a, 102b of the retractor body.

Second Alternate Embodiment of the Retractor

Figure 21:
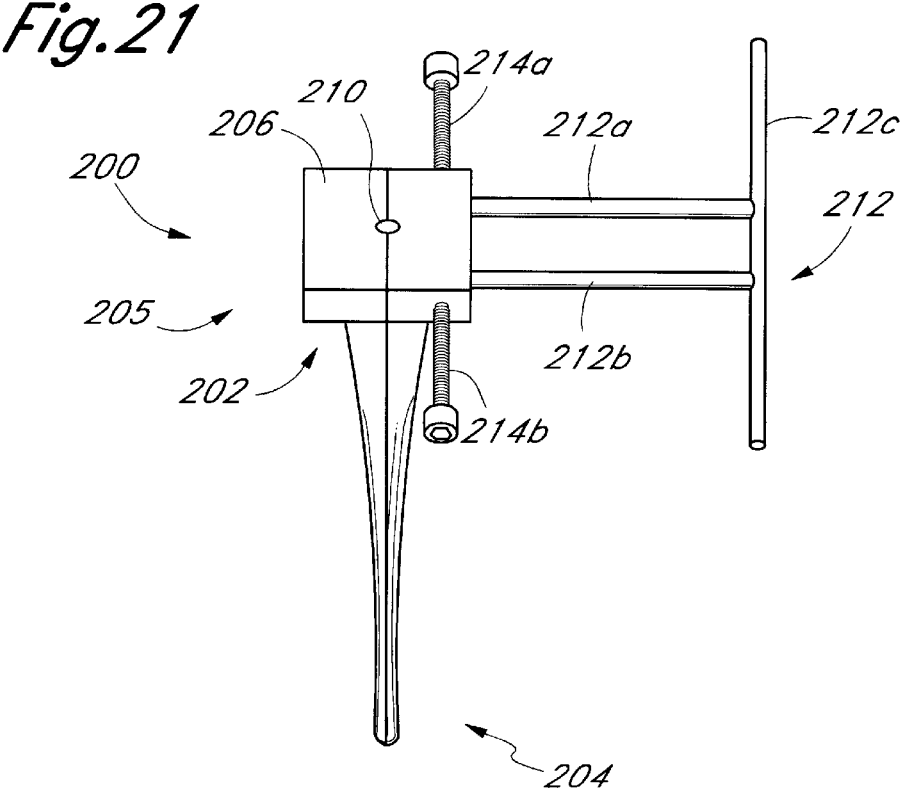
FIG. 21 is a perspective view of another alternate embodiment of a retractor in accordance with the present invention.
Figure 22:
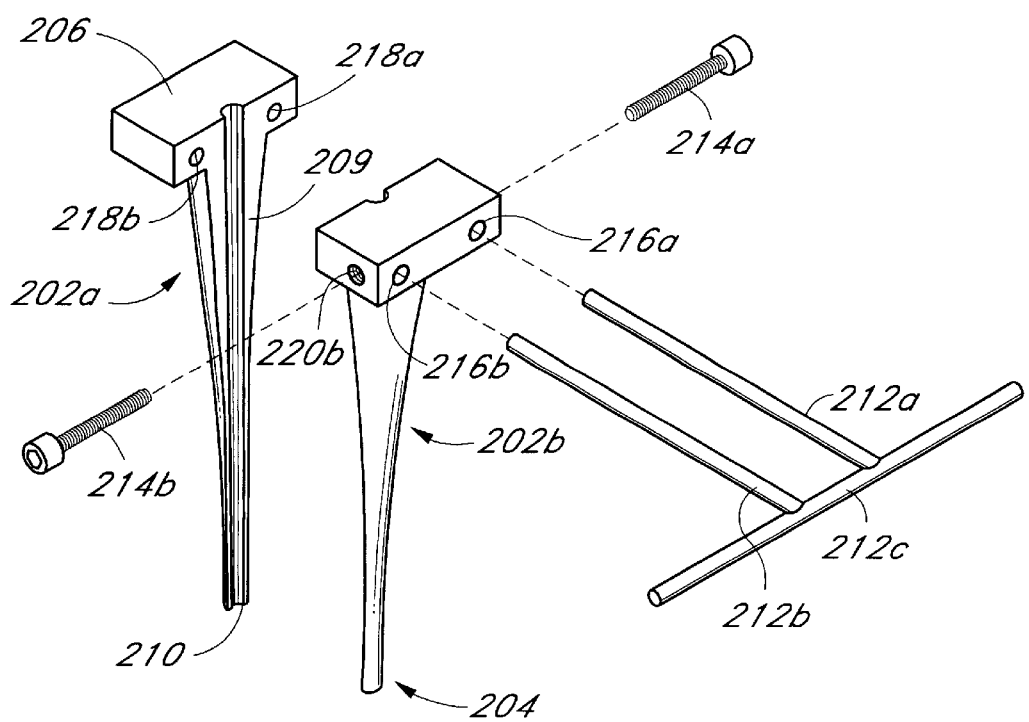
FIG. 22 is an exploded perspective view of the alternate embodiment of the retractor illustrated in FIG. 21.

Yet another embodiment of the retractor of the present invention is illustrated in FIGS. 21 and 22. The retractor 200 comprises a body portion 202 having a distal end 204, and a broader, collar portion 206 at its proximal end 205. Like the embodiment described above, this retractor 200 is formed in two halves 202a, 202b and preferably has a tapered distal end 204. Each half of the body of the retractor 202a, 202b, has a semi-circular groove 208 on its flat internal surface 209. When the two halves 202a, 202b are joined together, the semi-circular grooves 208 form a channel 210 running through the interior of the device 200, extending from the proximal end 205 to the distal end 204.

The collar 206 of the device 200 includes a pin assembly 212 comprising two parallel pins 212a, 212b attached at one end to a handle 212c, and two set screws 214a, 214b. As illustrated in FIG. 22, the pins 212a, 212b traverse guide passages 216a, 216b bored through the collar region 206 of one half of the retractor body 202b, and are insertable within holes 218a, 218b in the collar region 206 of the other half of the retractor body 202a, such that one half of the retractor body 202b can slide apart from the other half 202a on the pins 212a, 212b. The collar 206 also includes internally threaded holes 220a, 220b adapted to receive externally threaded set screws 214a, 214b. The set screw holes 220a, 220b enter the collar region 206 at right angles to the pin guide passages 216a, 216b such that when the set screws 214a, 214b are advanced, they tighten upon the pins 212a, 212b and thus, fix the distance between the two halves of the retractor body 202a, 202b.

Third Alternate Embodiment of the Retractor

Figure 28:
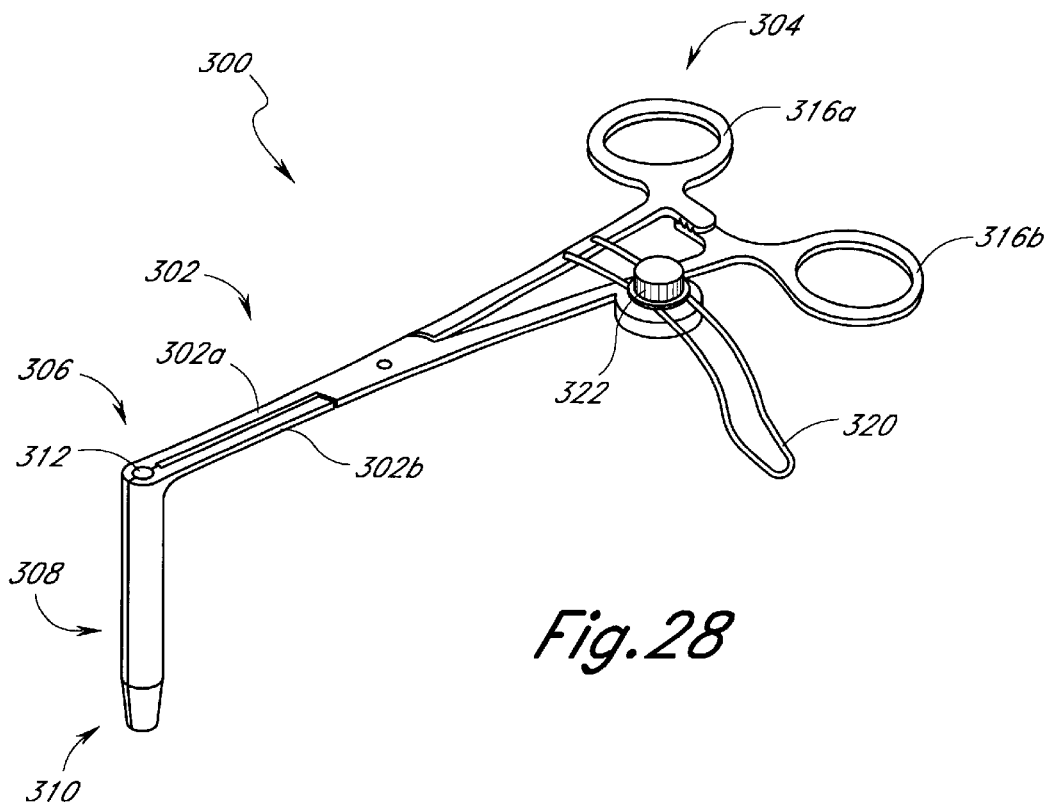
FIG. 28 is a perspective view of an alternate embodiment of a retractor of the present invention, shown in a closed position.
Figure 29:
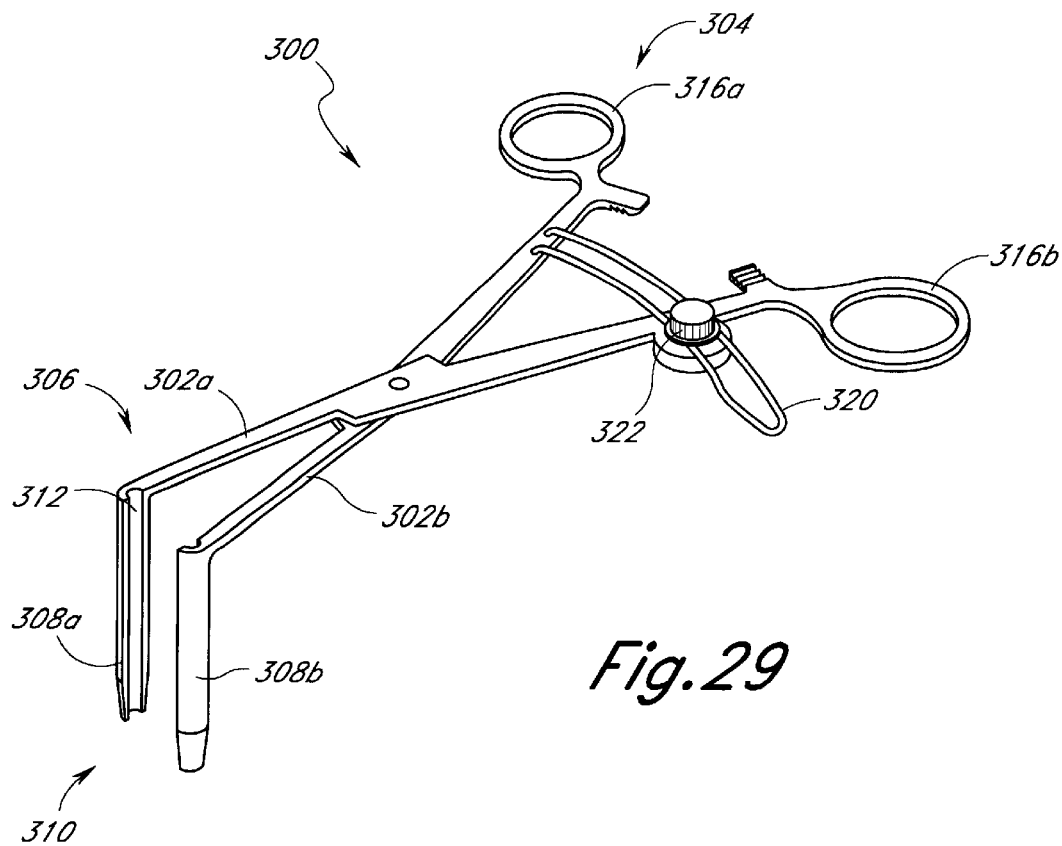
FIG. 29 is a perspective view of an alternate embodiment of a retractor of the present invention, shown in an open position.

Still another embodiment of the retractor of the present invention is illustrated in FIGS. 28 and 29. The retractor 300 comprises a distal body portion 302, and a proximal handle portion 304. The distal body portion 302 of the retractor 300 is formed in two portions or halves 302a, 302b. At the distal end 306 of the body portion 302, a retracting portion 308 extends away from, and at an angle to the body portion 302. Preferably, the retracting portion 308 extends substantially perpendicular to the body portion 302. The retracting portion 308 is also formed in two separable portions or halves 308a, 308b. Each of these portions 308a, 308b can be semi-circular in shape, or have a semi-circular groove 312 in its flat, internal surface (FIG. 29). The external surfaces are preferably rounded, and tapered toward the distal end 310. When the two portions 308a, 308b are brought together such that the two portions abut one another, as seen in FIG. 28, a channel 314 is formed through the interior of the retracting portion 308 of the retractor 300.

Handles 316a, 316b are located at the proximal end 304 of the retractor 300. The handles 316a, 316b are preferably elongate and of a dimension sufficient to permit manipulation by hand. The handles 316a, 316b are securely connected to the body portion 302 of the retractor 300. The handles 316a, 316b are used to control the movement of the retracting portion 308 of the retractor 300.

FIGS. 28 and 29 also illustrate a loop 320 extending from one of the handles 316a in the direction of the other handle 316b. The other handle 316b has a screw 322 inserted therethrough. The loop 320 surrounds the screw 322, such that when the screw 322 is tightened, the loop 320 is held securely between the screw 322 and the underlying surface. This mechanism acts to control the distance between the handles 316a, 316b thereby controlling the distance between the two halves of the retracting portion 308a, 308b. The handles 316a, 316b, and the corresponding retracting portions 308a, 308b may be locked into any position by sliding the loop 320 along the screw 322, then tightening the screw 322 to securely fix the loop 320 in the desired position. Of course, other locking mechanisms well known to those of skill in the art may also be used to control the positioning of the retractor 300.

The retractors of the present invention are preferably formed of one of many strong, biocompatible engineering polymers. Plastics such as polypropylene, polyethylene, or polyterephthalate, are preferred. Elastomers such as silastics or silicones can also be used. Most preferably, metals such as stainless or surgical steel, or titanium, are used to form the retractor.

Construction of the Dilator

Figure 11:
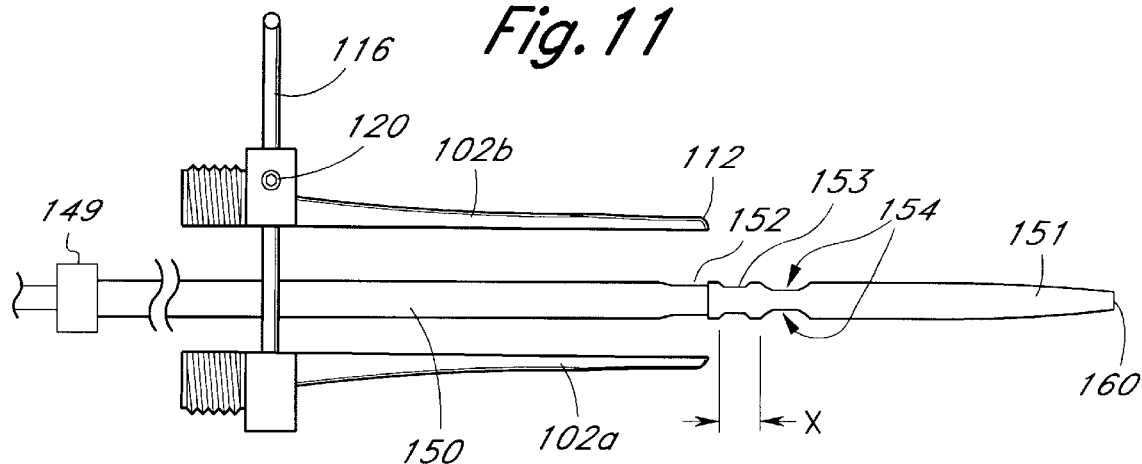
FIG. 11 is a side view of the 2 halves of the retractor of FIGS. 9 and 10 separated slightly and having a dilator inserted therethrough.
Figure 12:
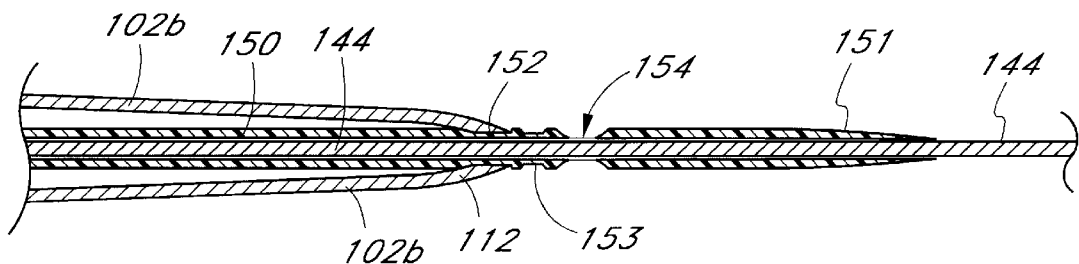
FIG. 12 is a cross-sectional view of the distal end of the retractor having a dilator and a guidewire inserted therethrough.
Figure 13:
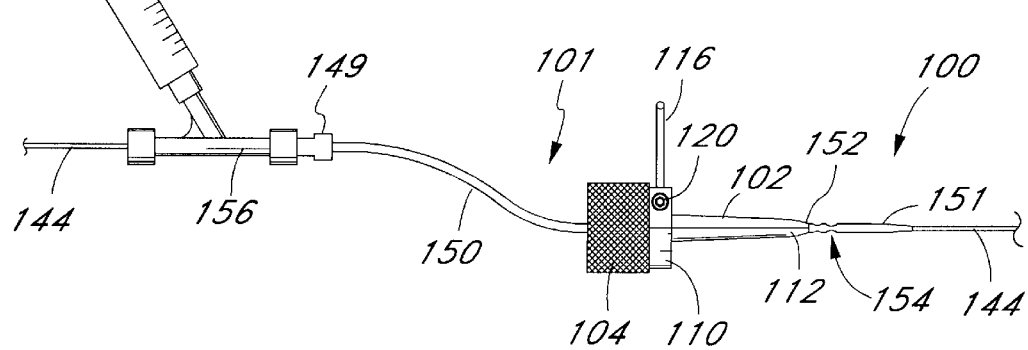
FIG. 13 is a side view of the components of the femoral artery localization and closure assembly.

As illustrated in FIGS. 11–13, the retractor 100 is preferably used in conjunction with a dilator 150. As is known to those of ordinary skill in the art, the hollow dilator 150 preferably includes a standard male connector 149, such as a Luer connector, at its proximal end and is narrowly tapered at its distal end 151. The inside diameter of the dilator channel 160 is large enough to accommodate a guidewire 144, so that the dilator 150 can be fed along the guidewire 144 and into the lumen of the femoral artery. Dilators are commonly used in procedures such as angioplasty and angiography to enlarge the puncture site and provide improved access to the femoral artery.

In one embodiment of the present invention, the dilator is preferably notched 152 near its distal end 151 around its entire circumference. This notch 152 provides a seat for the tapered distal tips of the two halves 102a, 102b of the retractor body, such that when the retractor 100 is closed upon the dilator 150, the sharp distal tip of the retractor body 112 is buried in the notch 152 of the dilator. This forms a smooth transition between the dilator 150 and retractor 100 (FIG. 12). As will be explained more fully below, when the guidewire 144 is inserted through the dilator 150 and the dilator 150 is then inserted through the retractor 100, (FIGS. 12–13), the dilator 150 lies securely within the interior circular channel 108 (FIG. 9) running the length of the retractor body 102.

The dilator 150 also preferably includes at least one indicator hole 154. The dilator 150 illustrated in FIGS. 11–13 includes two indicator holes 154 directly opposed to one another, located a few millimeters distal to the notch 152; the distance X between the holes 154 and the notch 152 is preferably only slightly larger than the thickness of the wall of the femoral artery.

Alternatively, a transducer-tipped pressure monitoring catheter, mounted to the outside of the dilator 150, may be used in conjunction with the dilator 150 and indicator holes 154. Use of the indicator holes 154 and pressure sensor will be described in detail below.

Dilator/Retractor Assembly

Another embodiment of the present invention comprises an entire femoral artery localization and closure assembly illustrated in FIG. 13. The guidewire 144 which emerges from the original puncture wound is fed through the dilator 150, and then the dilator 150 is inserted through the retractor 100. The retractor 100 is advanced along the dilator 150 until the distal tips of the retractor 112 stop within the notch 152 in the dilator 150. Preferably, the male fitting 149 on the proximal end of the dilator 150 is connected to one port of a commercially available 3-way Y-connector 156. A syringe 158 or other means of applying negative pressure is connected to one of the other ports on the Y-connector 156 and the proximal end of the guidewire 144 exits the Y-connector 156 via the remaining port. The Y-connector 156 therefore acts as a seal at the proximal ends of dilator 150 and guidewire 144.

Alternate Embodiments of the Dilator

Figure 17:
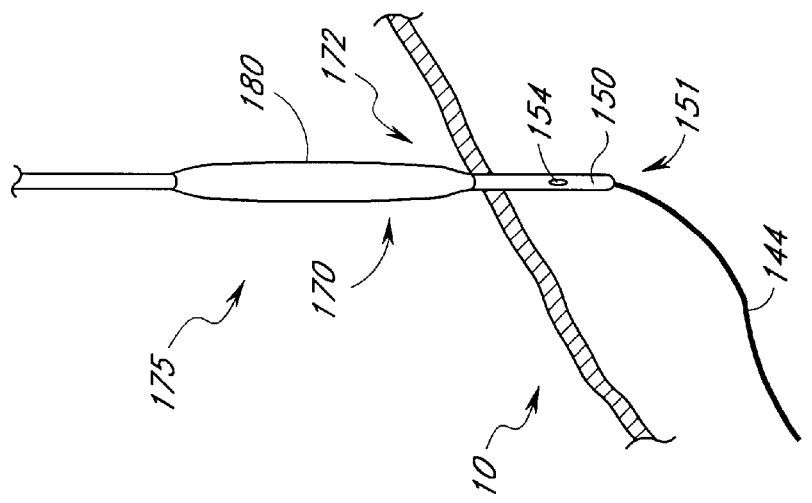
FIG. 17 is an enlarged perspective view of a dilator having a removable double-sleeved balloon at its distal end.

In another embodiment of the invention, a modified dilator 150 is used. As illustrated in FIG. 17, a double-sleeved balloon 170 is removably attached to the dilator 150 near its distal end 151, proximal to a single indicator hole 154. Preferably, the balloon 170 is placed a distance from the indicator hole 154 which is approximately the width of the arterial wall, e.g., about 1.5 mm. The inflatable, double-sleeved balloon 170 is angled at its distal end 172 to allow the balloon to better fit the femoral artery 10. The balloon 170 includes inflation means which allow the balloon to be inflated and deflated from the proximal end of the dilator 150. Use of the double-sleeved balloon 170 will be described in detail below.

In yet another embodiment, illustrated in FIGS. 23–25, the dilator 220 has both a double-sleeved balloon 222 and a second inflatable balloon 224 mounted on its distal end 226.

The double-sleeved balloon 222 is removably attached to the dilator 220 near its distal end 226, proximal to the single indicator hole 228. The second inflatable balloon 224 is mounted on the dilator 220 just distal to the indicator hole 228. When inflated, this second balloon 224 helps anchor the dilator 220 in place in the femoral artery 10, preventing the dilator 220 from being pulled out of the artery 10 during the procedure. Thus, the distal, second balloon 224 is positioned together with the indicator hole 228, within the artery 10, while the double-sleeved balloon 222, proximal to the indicator hole 228, remains outside of the artery 10 as illustrated in FIG. 25. The balloons 222, 224 assist in the proper positioning of the dilator 220, and help anchor the dilator 220 once it is properly positioned, as will be explained in detail below.

The inner sleeve 230 of the double-sleeved balloon 222 is preferably shaped to facilitate the insertion of the retractor 200 between the two sleeves 229, 230, as will be described in more detail below. As illustrated in FIG. 24, the inner sleeve 230 can be in the shape of an "I", thus providing additional space between the inner surface of the outer sleeve 229, and the outer surface of the inner sleeve 230. This allows the two halves of the retractor body 202a, 202b to be inserted between the two sleeves 229, 230 more easily. The two sleeves of the balloon 229,230 can be shaped in any form that would help facilitate insertion of the retractor 220.

The dilator 200 having both a double-sleeved balloon 222 and a second, distal balloon 224, is further illustrated in FIG. 26. As can be seen from the drawing, the dilator 200 has 4 different lumens 232, 234, 236, 238 extending from the proximal end of the dilator 225 to the distal end of the dilator 226. A guidewire 240 is inserted through one of the lumens 236. Another lumen 232 is used to inflate the double-sleeved balloon 222, while a third lumen 238 is used to inflate the second balloon 224 at the distal end of the dilator 226. The fourth lumen 234 is used to aspirate blood through the indicator hole 228 at the distal end of the dilator 226. Syringes are preferably used to provide the aspiration and inflation pressure through these lumens 232, 234, 236, 238. The proximal end of the dilator 225 is preferably adapted to allow for fluid communication between the syringes and the various lumens 232, 234, 236, 238 in the dilator. Of course, other means of aspirating blood and inflating the balloons may also be used, and connectors specifically adapted for these devices can be attached at the proximal end of the dilator 225 to accommodate the means chosen.

Dual Lumen Catheter

Figure 30:
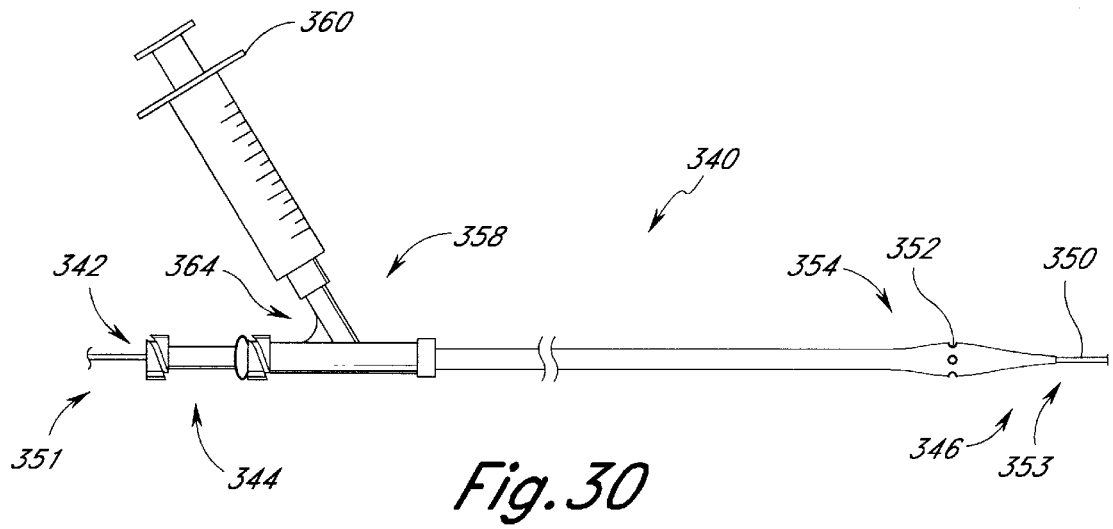
FIG. 30 is a side view of a dual-lumen indicator tube of the present invention, having a guidewire inserted through its central lumen.
Figure 31:
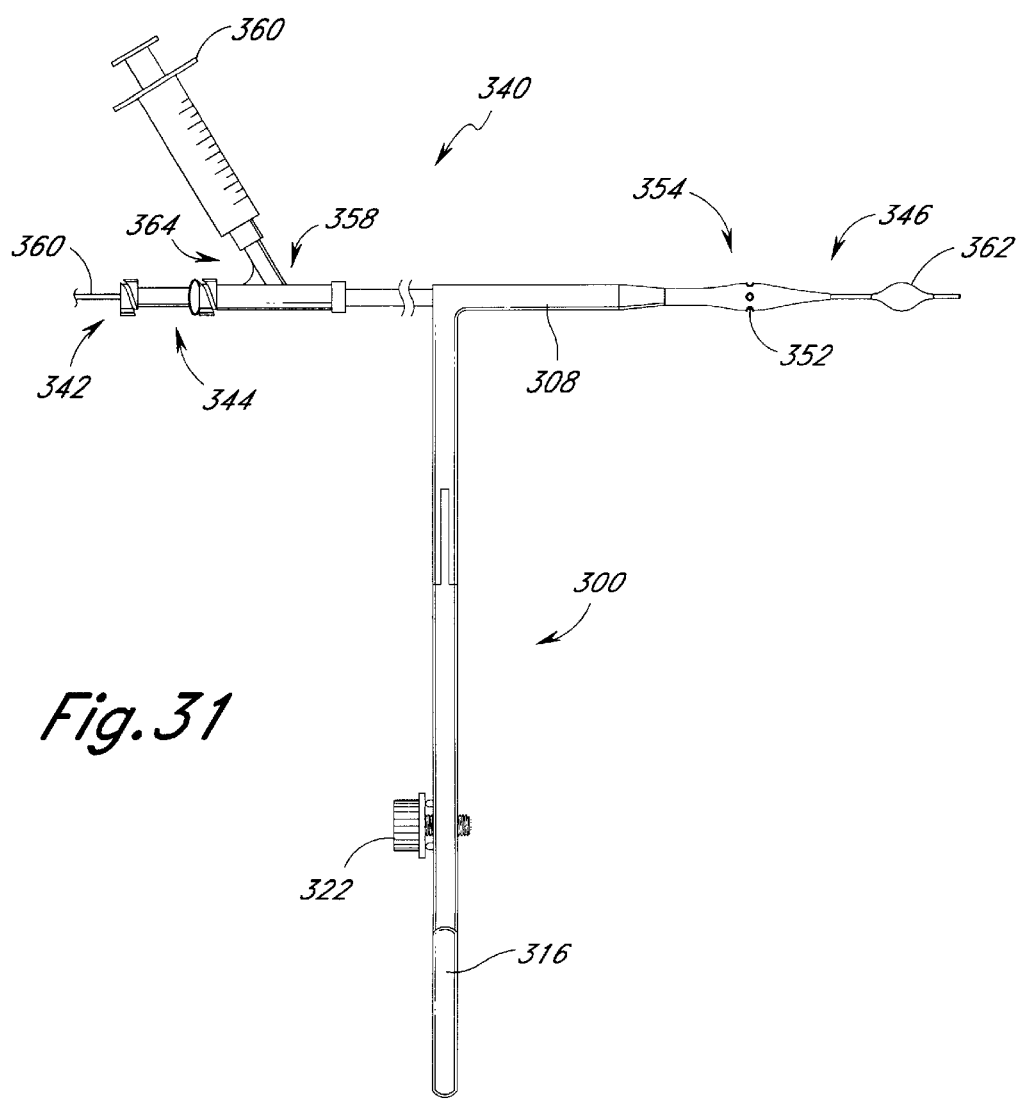
FIG. 31 is a side view of the dual-lumen indicator tube of the present invention, with the retractor mounted thereon.

In yet another embodiment of the invention, a dual-lumen catheter is used to locate the exact site of the puncture wound. As illustrated in FIGS. 30 and 31, the catheter 340 has an inner lumen 342 which extends from the proximal end of the catheter 344 all the way to the distal end of the catheter 346. This inner lumen 342 is adapted to receive an inner catheter 360 or guidewire 350, as will be explained in more detail below.

The outer lumen of the dual-lumen catheter 340 surrounds the inner lumen 342, and also extends from the proximal end of the catheter 344 to the distal end 346. Near the distal end of the catheter 346, at least one indicator hole 352 is positioned in the outer wall of the catheter 340. The indicator hole 352 provides fluid communication between the area outside of the catheter 340 and the outer lumen. The outer surface of the catheter 354 surrounding the indicator hole 352 is preferably raised, acting as a stop. Preferably, the distance between the indicator hole 352 and the proximal end of the raised surface of the retractor 354, is approximately the same as the thickness of the wall of the femoral artery. As will be explained below, the retractor 300 is first mounted on the distal end of the catheter, and positioned such that the distal tip of the retracting portion 310 stops just proximal to the raised surface 354, about 0.5 mm proximal to the indicator hole 352. This assures that the distal tip of the retracting portion 310 will be properly positioned inside the patient's body at the site of the wound in the artery.

At the proximal end of the catheter 344, the proximal end 358 of the outer lumen is preferably joined to a connector 364, such as a Luer-type connector, which is adapted to receive a syringe 360 or other source of negative pressure, as will be explained in more detail below.

The Surgical Clip Applicator

Figure 5:
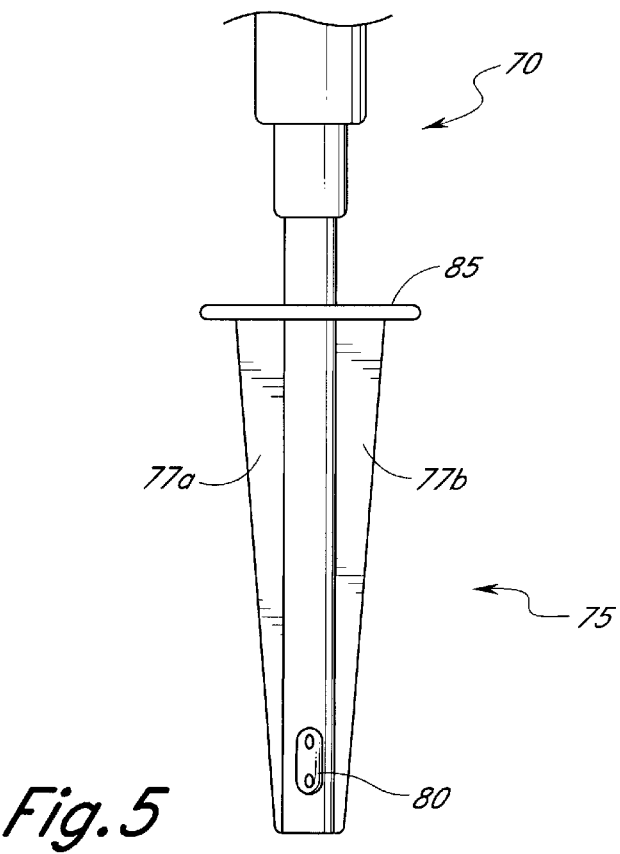
FIG. 5 is a side view of the distal end of a surgical clip applicator to be used in conjunction with the wound closure device of the present invention.

The retractor of the present invention is used to facilitate closure of wounds to the vasculature of a patient using surgical clips, staples, or sutures. One aspect of the present invention therefore includes the use of a surgical clip applicator 70. A surgical clip applicator 70 for use with the retractor 30 of the present invention is illustrated in FIG. 5. As shown in this figure, the distal end of the clip applicator 75 is fitted with two triangular protrusions or wings 77a, 77b that extend laterally from the sides of the distal end of the clip applicator 75. These wings 77a, 77b are configured to fit within the grooves 65 located on the interior surface of the two halves 35a, 35b of the body of the retractor 30, as is best seen in FIG. 8. With the wings 77a, 77b of the clip applicator 70 in the grooves 65 in the two halves of the body of the retractor 35a, 35b, the clip applicator 70 is guided into proper position within the patient's body, as will be discussed in more detail below. In addition, the surgical clip applicator 70 preferably has a guide 80 attached to its distal end 75. The guide 80 preferably extends laterally from the side of the clip applicator 70, and is open at its proximal and distal ends such that a guidewire 20 may be threaded therethrough. This guide 80 is used in combination with the guidewire 20 to accurately guide the clip applicator 70 to the site of the vascular puncture 25, as will be described below.

The surgical clip applicator 70 preferably also has a stop 85 located proximal of the distal end 75, at the point where the proximal ends of the wings of the applicator 77a, 77b end. As will be explained, the stop 80 also aids in the proper positioning of the clip applicator 70 at the site of the vascular puncture 25, and prevents the clip applicator 70 from being inserted too far into the patient's body.

Alternate Surgical Clip Applicator Assembly

Figure 14:
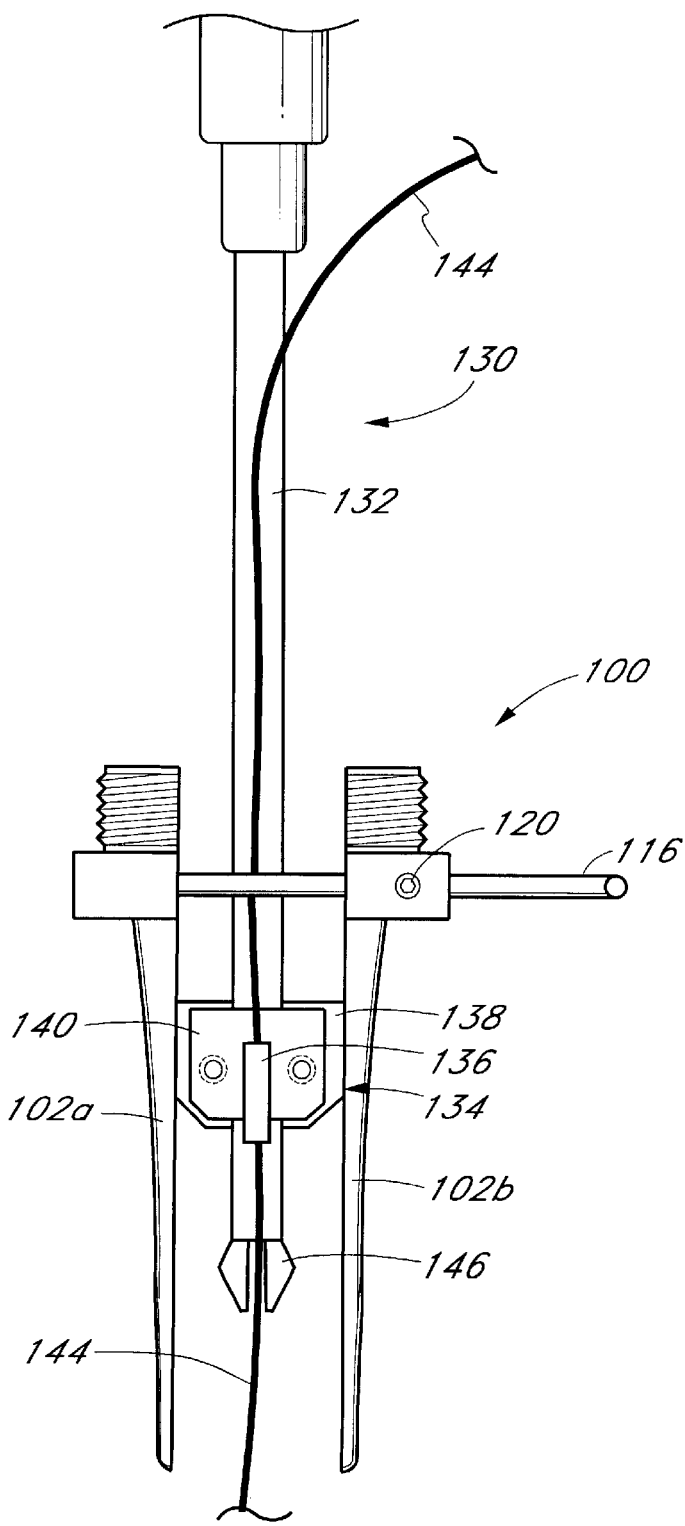
FIG. 14 is a side view of the 2 halves of the retractor separated slightly and having a surgical clip applicator with an applicator guide and a guidewire inserted therethrough.
Figure 15:
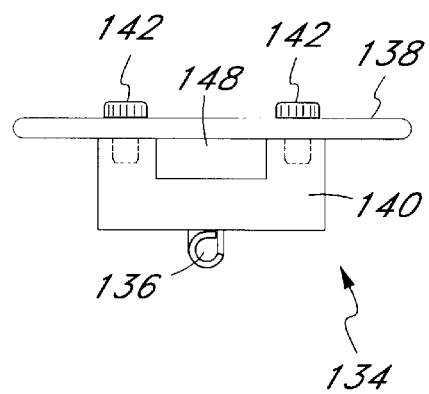
FIG. 15 is a top view of the surgical clip applicator guide of the present invention.
Figure 16:
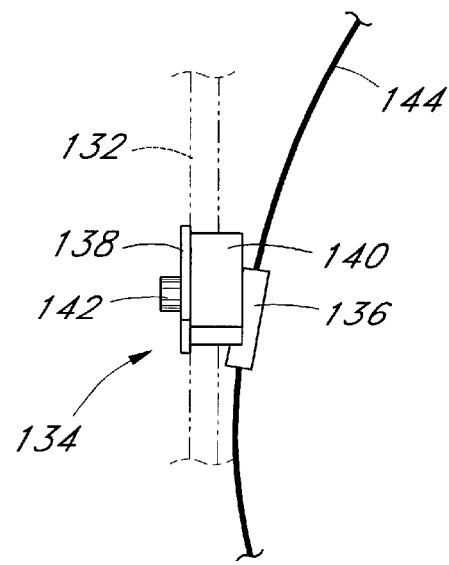
FIG. 16 is a side view of the clip applicator guide, having a guidewire inserted therethrough.

Referring now to FIGS. 14–16, there is illustrated an alternate embodiment of a surgical clip applicator assembly 130. The clip applicator assembly 130 incorporates a standard commercially available surgical clip applicator 132. In accordance with the present invention, the applicator is modified to include a guide assembly 134 reversibly fastened near its distal end. The guide assembly comprises a winged guide plate 138 which is reversibly secured to a body 140. In the embodiment illustrated in FIGS. 14–16, allen screws 142 are used to attach the guide plate 138 but other well known means of attachment can also be used. The distal end of the surgical clip applicator 132 slides within the channel 148 (FIG. 15) formed when the winged guide plate 138 is fastened to the guide body 140.

Attached to the guide body 140 is a guidetube 136 which is adapted to accept the guidewire 144. A preferred embodiment of said guidetube 136 includes a mechanism to close the guidetube 136 once the guidewire 144 has entered. Such a mechanism may involve a second partially open tube which fits within said guidetube 136. This second tube can be rotated within the guidetube 136 to open the guidetube 136 when the openings in both tubes are aligned or close the guidetube 136 when the openings of the tubes are offset. To facilitate the opening and closing, the inner tube preferably includes a handle that passes through a slot in the outer guidetube 136. This mechanism can be spring-loaded like the closures commonly used on pieces of jewelry.

The surgical clip applicator guide assembly 134, together with the retractor 100 and the guidewire 144, is designed to accurately guide the clip applicator 132 to the site of the femoral artery puncture as detailed below. As explained above, the lateral edges of the winged guide plate 138 are configured to fit within the groove 126 (FIG. 10) located on the interior surface of each half of the retractor body 102a, 102b. The surgical clip applicator 132 is guided between the retracted halves of the retractor body 102a, 102b following the guidewire 144 which passes through the guidetube 136 at the distal most end of the surgical clip applicator 132.

Second Alternate Surgical Clip Applicator Assembly

An alternate embodiment of the surgical clip applicator assembly 250 is illustrated in FIG. 27. Again, the clip applicator assembly 250 incorporates a standard commercially available surgical clip applicator 252. The applicator 252 is modified to include a guide assembly 254 reversibly fastened near its distal end 256. The guide assembly 254 is adapted to receive an indicator tube 260. The indicator tube 260 is a hollow tube having an indicator hole 264 near its distal end 262. The indicator tube 260 is adapted to receive a guidewire 240 therethrough, and to be connected to a source of negative pressure at its proximal end. This source of negative pressure, such as a syringe, is used to provide aspiration through the indicator hole 264. When properly positioned on the clip applicator 252, the distal end of the indicator tube 262 and the indicator hole 264 extend past the distal end of the clip applicator 256. Preferably, the distance between the indicator hole 264 and the distal tip of the clip applicator 256 is approximately equal to the width of the arterial wall, e.g., about 1.5 mm.

Methods of Use

Referring first to FIGS. 4–8, a first method of use of the retractor 30 in conjunction with a surgical clip applicator 70 to close a wound 25 in the femoral artery 10 will now be described. As noted above, during angioplasty or angiography, the femoral artery 10 is first punctured with a hollow needle 15 and a guidewire 20 is inserted therethrough (FIG. 4). A proximal portion of the guidewire 21 remains outside the patient's body. After the distal end of the guidewire 23 is in position within the femoral artery 10, the hollow needle 15 is removed. A catheter (not shown) is then threaded over the guidewire 20, and inserted into the patient's body.

In a preferred embodiment, a specially designed guidewire 20 having an inflatable balloon 24 located near its distal end 23 is used for the diagnostic or therapeutic procedure. The guidewire 20 is threaded through the hollow needle 15 and into the patient's vasculature. Alternatively, such as for balloon angioplasty procedures, a standard guidewire well known to those of skill in the art can be used in conjunction with a balloon catheter. The balloon on the distal end of the catheter can be used in place of the balloon 24 located on the guidewire 20.

Following completion of the therapeutic or diagnostic procedure, the catheter used during the procedure is removed. The guidewire 20 remains in place in the patient's vasculature. (Note that when a balloon catheter is used in place of a guidewire having a balloon on its distal end, the catheter is left inside the patient, and use of its balloon is identical to the use of the balloon 24 on the guidewire 20 described below).

When the physician desires to close the wound 25 in the femoral artery 10, he or she first withdraws the guidewire 20 and/or catheter through the patient's vasculature using the portion of the guidewire 20 and/or catheter that remains outside the patient's body 21, until the distal end 23 of the guidewire 20 and/or catheter is within the femoral artery 10 close to the femoral artery puncture site 25. The balloon 24 on the distal end 23 of the guidewire 20 or catheter is then inflated, and the guidewire 20 or catheter is withdrawn further until the physician feels some resistance. This will indicate that the balloon 24 is inside the femoral artery 10 and at the site of the puncture wound 25. The physician then threads the proximal end of the guidewire 21 into the hole 49 located at the distal end 37 of the fully assembled retractor 30 (FIGS. 2, 3 and 6). The guidewire 20 is threaded through the channel 50 formed in the body of the retractor 35, until the proximal end of the guidewire 21 emerges through the hole 47 in the cap 40 at the proximal end of the retractor 41 (FIG. 6). The retractor 30 is then slowly advanced along the guidewire 20 and into the patient's body, until resistance is felt. This resistance indicates that the distal tip of the retractor 37 is contacting the inflated balloon 24 in the femoral artery 10. The distal tip of the retractor 37 therefore will be properly located at the site of the puncture in the femoral artery 25, as is shown in FIG. 6.

In a preferred embodiment, the guidewire 20 used in conjunction with the femoral artery closure retractor 30 has a marking 27 on it which also helps to indicate when the retractor 30 has been properly positioned (FIG. 6). This marking 27 preferably consists of a tiny bead or colored line on the guidewire 20. The marking on the guidewire 27 is placed proximal of the proximal end of the balloon 26. The length of the retractor 30 is measured, and the marking 27 is made at least that same length in a proximal direction on the guidewire 20, measured from the proximal end of the balloon 26. Thus, when the retractor 30 is advanced over the guidewire 20 and resistance is felt, the physician checks to see if the marking on the guidewire 27 has emerged through the proximal end of the retractor 41, as is illustrated in FIG. 6. If the marking 27 is not yet visible, the physician must advance the retractor 30 further to ensure that it contacts the femoral artery puncture site 25.

Once the retractor 30 is properly positioned within the patient's body, the surgical clip applicator 70 or other method of closing the puncture wound 25 is used. The cap 40 on the retractor 30 is first removed from the body by unscrewing (FIG. 3). The proximal end of the guidewire 21 emerging from the proximal end of the retractor 41 is threaded through the guide 80 located on the outer surface of the applicator 70, as illustrated in FIG. 7. The wings on the surgical clip applicator 77a, 77b are inserted into the hole 90 formed at the proximal end of the body of the retractor 39, by lining up the wings 77a, 77b on the applicator 30 with the grooves 65 located on the inner surface 67 of the retractor body halves 35a, 35b (FIGS. 7 and 8). The wings on the clip applicator 77a, 77b are sized to fit within the grooves 65 of the retractor 30, as is best illustrated in FIG. 8. The clip applicator 70 is then advanced, which causes the two halves of the body of the retractor 35a, 35b to separate, as shown in FIG. 7. As the two halves 35a, 35b separate, the patient's tissue is displaced laterally, allowing better access to the puncture site 25 in the femoral artery 10 below the overlying tissues. The clip applicator 70 is advanced through the retractor 30 until the stop on the applicator 85 contacts the proximal end of the retractor 39. At this time, the balloon on the guidewire 24 or catheter is deflated, and the catheter and/or guidewire 20 is removed from the patient. The surgical clips located at the distal tip of the clip applicator 75 are applied to the puncture wound 25, using the method well known to those of ordinary skill in the art. Once the femoral artery puncture wound 25 is closed, the clip applicator 70 and retractor 30 are removed from the patient.

First Alternate Method

Referring now to FIGS. 9–16, a method of using the alternate embodiment of the retractor 100 in conjunction with the dilator 150 and surgical clip applicator assembly 130 to localize and close the femoral artery puncture wound is now described. As described above, following completion of the angioplasty or angiography, the catheter used during the procedure is removed from the patient's body, leaving only the guidewire threaded into the femoral artery. If desired, before the retractor-dilator assembly 101 (FIG. 13) is used, a standard dilator of a smaller diameter than that 150 incorporated into the retractor-dilator assembly 101 can be fed onto the proximal end of the guidewire and advanced down the guidewire and into the artery. This preliminary step dilates the overlying tissue if necessary, making it easier to subsequently pass the larger retractor-dilator assembly 101 through the surrounding tissue.

If the tissue has been dilated as above, the smaller bore standard dilator is first removed. The proximal end of the guidewire 144 is first inserted into the distal channel 160 (FIG. 11) of the dilator 150. The dilator 150 has been previously inserted through the internal channel of the retractor 100, and the retractor 100 advanced over the dilator 150 until the distal tip 112 comes to rest in the notch 152 on the distal tip of the dilator 150. The Y-connector 156 is then attached to the proximal end of the dilator 150 and a syringe 158 attached to one of the ports of the connector 156. The retractor-dilator assembly 101 is then advanced over the guidewire 144 into the patient's body.

While the retractor-dilator assembly 101 is advanced into the patient's body, suction is continuously applied via the syringe 158 or other means of negative pressure (FIG. 13) to the dilator 150. At the moment the indicator holes 154 enter the lumen of the femoral artery, blood is aspirated into the syringe 158, indicating that the dilator 150 has been inserted through the puncture site into the femoral artery. Thus, the distal tip of the retractor 112, still buried within the notch 152 in the dilator 150, is located just proximal or outside the artery wall at the site of the puncture wound and the indicator holes 154 in the dilator 150 are located just distal or inside the artery lumen.

Alternatively, the dilator 150 includes a pressure sensor (not shown) such as a fiber optic pressure sensor, near its distal tip. The sensor is preferably mounted to the outside wall of the dilator 150. In a preferred embodiment, a transducer-tipped pressure monitoring catheter, such as the Camino Catheter available from Camino Laboratories, San Diego, Calif., is used. The pressure sensor, mounted on the outside of the dilator 150, is inserted over the guidewire 144 and into the femoral artery. The pressure sensor, in conjunction with a pressure monitoring system, will indicate an increase in pressure when it is inserted into the femoral artery. At that point, the advancement of the retractor 100 is stopped, such that the distal tip of the retractor 112 is located just proximal the artery wall 10 at the site of the puncture wound. This allows the physician to properly locate the site of the femoral artery puncture wound in the patient.

Once the dilator 150 and retractor 100 are in proper position, the cap 104 is removed from the retractor 100 and the two halves 102a, 102b of the retractor body are separated slightly (FIG. 10) by loosening the set screws 120a, 120b and sliding the two halves 102a, 102b of the retractor laterally away from one another. This causes the distal tips 112 of two halves 102a, 102b to emerge from the notch 152 in the dilator 150 (FIG. 11) and straddle the puncture site. The set screws 120a, 120b, are then tightened to hold the two halves 102a, 102b of the retractor 100 in this separated position. While pressing the retractor 100 down against the outer wall of the femoral artery, the dilator 150 is withdrawn, leaving only the retractor 100 and the guidewire 144 in position at the site of the puncture wound in the artery.

To close the wound, the retractor 100 must be retracted far enough to allow the surgical clip applicator assembly 130 to access the puncture site. Upon loosening the set screws 120a, 120b, the two halves 102a, 102b of the retractor are further separated by applying pressure on the retractor pin handle 116c (FIGS. 9–10). When sufficiently retracted, the set screws 120a, 120b on the retractor assembly 100 are tightened to maintain the proper distance between the retractor halves. If necessary, a separate retractor, having a thickness suited for sliding within the grooves 126 in each half 102a, 102b of the retractor body, and a width equal to that of the winged guide plate 138 (FIG. 14) of the surgical clip applicator guide assemble 134, can be used to open the retractor body to the proper distance.

Second Alternate Method

In an alternate embodiment illustrated in FIG. 17, the modified dilator 150 having a double-sleeved inflatable balloon 170 removably attached to the distal end of the dilator 151, just proximal to the indicator hole 154, is used. The balloon dilator apparatus 175 is inserted over the guidewire 144 into the patient's body. As described above, as the balloon-dilator apparatus 175 is advanced, negative pressure is applied to the system via the syringe or other source. The advance of the balloon-dilator apparatus 175 is stopped as soon as blood is aspirated. The double-sleeved balloon 170 is then inflated to form a tunnel 176 between the femoral artery puncture wound and the surface of the patient's body, as illustrated in FIG. 18.

The double-sleeved balloon 170 advantageously prevents the femoral artery closure retractor 100 from entering the femoral artery 10 and damaging it. Should the deflated balloon 170 be advanced into the femoral artery 10, the process of inflating the balloon 170 will pull the balloon 170 out of the artery 10, thereby safely creating a tunnel 176 used to access the artery 10.

Figure 19:
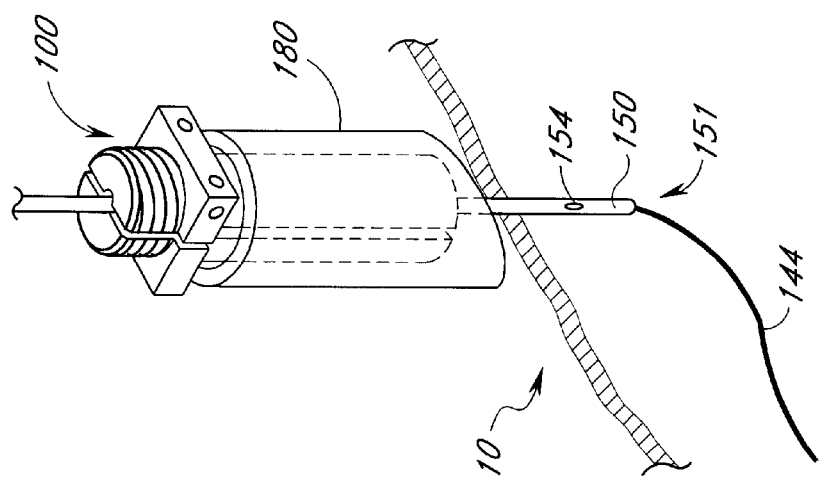
FIG. 19 is an enlarged perspective view of the dilator of FIG. 18 having the retractor inserted between the sleeves of the balloon.
Figure 18:
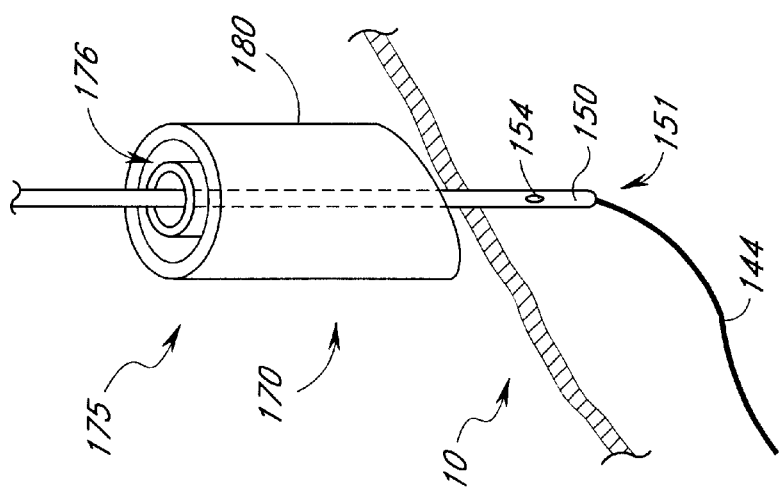
FIG. 18 is an enlarged perspective view of the dilator of FIG. 17 with the sleeves of the balloon inflated.

The balloon 170 is preferably angled at its distal end 172 to allow the balloon 170 to "fit" the femoral artery 10, as shown in FIGS. 17–19.

Once the balloon 170 is inflated (FIG. 18) the retractor 100 is advanced between the two sleeves of the balloon 170, until the distal tip of the retractor 112 reaches the distal end of the double sleeved balloon 170. Once the retractor 100 is positioned between the two sleeves of the balloon 170, the two halves of the retractor 102a, 102b are moved laterally away from one another, as described above. The inner sleeve 178 and the dilator 150 are removed from the patient, leaving the separated retractor 100 and the outer sleeve 180 of the balloon 170 in the patient. The dilator 150 and the inner sleeve 178 are removed from the patient along the guidewire 144.

Figure 20:
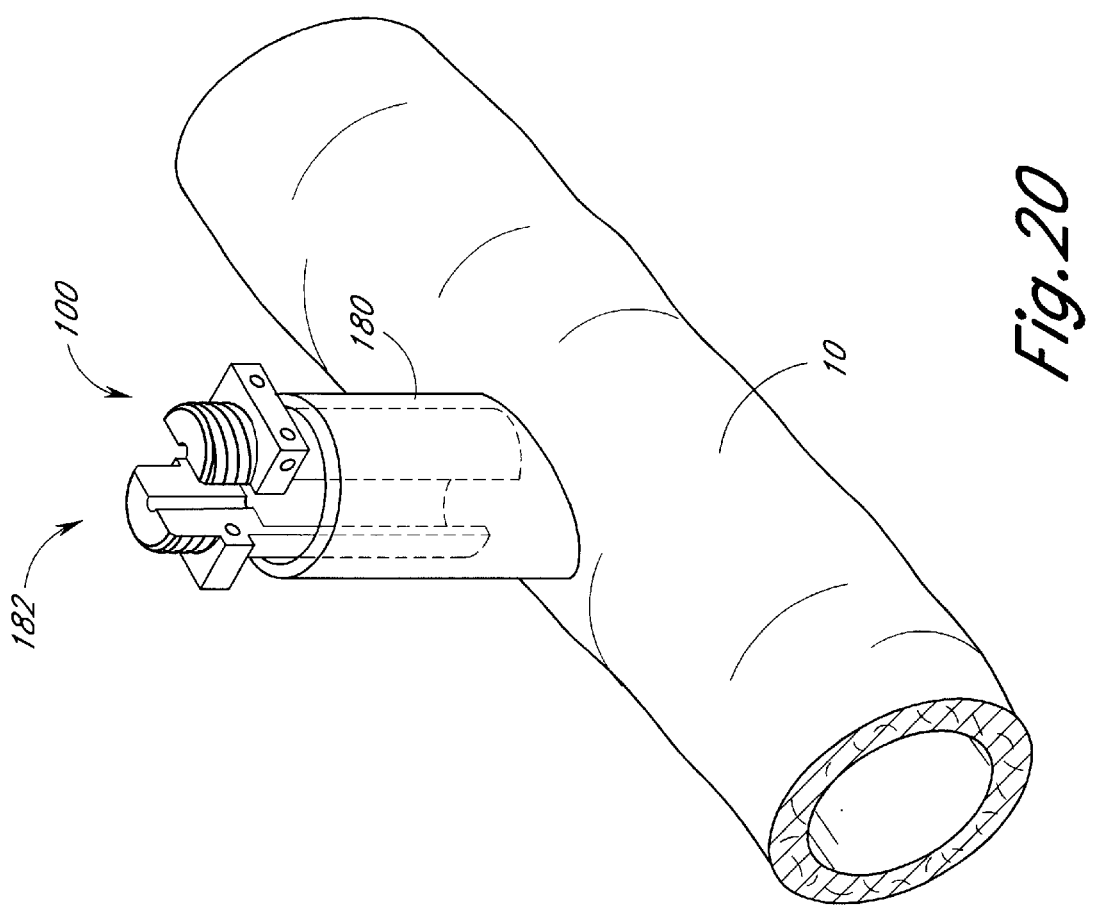
FIG. 20 is an enlarged perspective view of the dilator and retractor of FIG. 19 with the dilator removed, illustrating the tunnel formed by the retractor and the outer sleeve of the balloon.

The retractor 100 and the outer sleeve of the balloon 180 form an access tunnel 182 between the femoral artery puncture wound and the surface of the patient's body, as illustrated in FIG. 20. This tunnel 182 allows for the introduction of the wound closure device to seal the femoral artery puncture wound.

At this point, with the retractor providing access to the femoral artery, the proximal end of the guidewire 144 is inserted into the guidetube 136 on the surgical clip applicator assembly 130 and the wings on the guide plate are fitted within the grooves 126 of the opened retractor body 102 (FIGS. 14–16). The clip applicator assembly 130 can now be advanced toward the puncture wound, sliding within the grooves 126 in the retractor body 102, guided by the guidewire 144 passing through the guidetube 136 at the distal tip of the surgical clip applicator assembly 130. When the distal tip of the surgical clip applicator 130 has reached the outer wall of the femoral artery 10, at the site of the puncture wound, the surgeon withdraws the guidewire 144 from the patient's body and immediately deploys a surgical clip. A second clip can then be deployed a millimeter or two away from the first clip in order to ensure that the wound is closed.

In a preferred embodiment, just prior to closure of the puncture site, the flexible guidewire 144 used during the primary procedure is replaced with a commercially available guidewire that can become rigid at its distal end, forming a hook. The hooked distal end can be pulled back, "hooking" the puncture wound in the artery. As the guidewire is pulled back further, the puncture wound is stretched into a linear slit, making it more amenable to closure by surgical clips.

Third Alternate Method

Referring now to FIGS. 21–27, a method of using the alternate embodiment of the retractor 200 in conjunction with the dilator 220 and surgical clip applicator assembly 250 to localize and close the femoral artery puncture wound is now described. As described above, following completion of the angioplasty or angiography, the catheter used during the procedure is removed from the patient's body, leaving only the guidewire 240 threaded into the femoral artery 10.

The proximal end of the guidewire 240 is first inserted into the distal lumen 236 (FIG. 26) of the dilator 220. The dilator 220 is advanced over the guidewire 240 into the patient's body. As described above, as the balloon-dilator apparatus 250 is advanced, negative pressure is applied to the system via the syringe or other source connected at the proximal end of the dilator 225. The advance of the dilator 220 is stopped as soon as blood is aspirated through the indicator hole 228, thus indicating that the distal end of the dilator 226 is positioned within the femoral artery 10. The distal balloon 224 and the double-sleeved balloon 222 are then inflated to anchor the dilator 220 in place and to form a tunnel between the femoral artery puncture wound and the surface of the patient's body.

Once the balloons 222, 224 are inflated, the retractor 200 is advanced between the two sleeves 229, 230 of the double sleeved balloon 222. As illustrated in FIG. 24, the inner sleeve 230 of the double sleeved balloon 222 can be in an "I" shape, which provides more space between the two sleeves to insert the two halves 202a, 202b of the reactor 200. The retractor 200 is advanced between the two sleeves 229, 230, as described above, until the distal tip of the retractor 204 is positioned just proximal to the puncture wound in the femoral artery 10.

Once the retractor 200 is positioned between the two sleeves of the balloon 229, 230, the two halves of the retractor 202a, 202b are moved laterally away from one another. This is done by loosening the set screws 214a, 214b, and sliding one half of the retractor body 202b away from the other half 202a on the pins 212a 212b. The inner sleeve 230 of the double-sleeved balloon 222 and the dilator 220 are removed from the patient along the guidewire 240, leaving the separated retractor 200 and the outer sleeve 229 of the balloon 222 in the patient. The retractor 200 and the outer sleeve of the balloon 229 form an access tunnel between the femoral artery puncture wound and the surface of the patient's body. This tunnel allows for the introduction of the wound closure device to seal the femoral artery puncture wound.

At this point, with the retractor 200 and outer sleeve of the balloon 229 providing access to the femoral artery 10, the proximal end of the guidewire 240 is inserted into the distal end 262 of the indicator tube 260 which is mounted on the surgical clip applicator 252. As described above, the distal end 262 of the indicator tube 260 having an indicator hole 264 in it is positioned so that the indicator hole 264 extends past the distal end 256 of the clip applicator 252. The indicator tube 260 and the clip applicator 252 are advanced over the guidewire 240 while aspiration pressure is applied to the proximal end of the indicator tube 260. As soon as blood is aspirated through the indicator hole 264, the advancement of the indicator tube 260 and clip applicator 256 is stopped. At this point, the distal end of the surgical clip applicator 256 is positioned at the site of the puncture wound in the femoral artery 10. Surgical clips are then applied to seal the wound.

Preferably, the distal end of the indicator tube 262 is curved or hooked. The hooked distal end is used to hook the puncture wound in the artery, bringing the edges of the wound together to facilitate application of the clip. Using the hooked distal end 262 of the indicator tube 260, the puncture wound is stretched into a linear slit, making it more amenable to closure by surgical clips.

Fourth Alternate Method

Referring now to FIGS. 28–31, still another method of closing a wound in the femoral artery of a patient will be described. Here again, the femoral artery is first punctured with a hollow needle and a guidewire 350 is inserted therethrough. A proximal portion of the guidewire 351 remains outside the patient's body. After the distal end of the guidewire 353 is in position within the femoral artery, the hollow needle is removed. Diagnostic and/or therapeutic procedures are then carried out, using the guidewire 350 to guide the insertion of the other medical instruments into the vasculature of the patient.

Following completion of the therapeutic or diagnostic procedure, the devices used during the procedure are removed. The guidewire 350 remains in place in the patient's vasculature. When the physician desires to close the wound in the artery, he or she first mounts the retractor 300 on the distal end of the dual-lumen catheter 340. This is done by loosening the screw 322 on one of the handles 316b, and moving the handles 316a, 316b away from one another to separate the two halves of the retracting portion 308, and the two parts of the retracting portion 308a, 308b are positioned around the dual-lumen catheter 340. The dual lumen catheter 340 fits within the semicircular channel or grooves 312 formed in the inner surface of the retracting portion 308 of the retractor 300. The two halves of the retracting portion 308a, 308b are brought together using the handles 316a, 316b to surround the catheter 340. The retracting portion 308 is positioned on the catheter 340 just proximal to the raised portion of the catheter 354, so the distal tip of the retracting portion 310 is located just proximal to the indicator hole 352. Preferably, the distal tip of the retracting portion 308 will be approximately 0.5 mm behind the indicator hole 352 (see FIG. 31). Once in position, the screw 322 is tightened on the loop 320 to lock the two parts of the retracting portion 308a, 308b in position on the catheter 340.

Once the retractor 300 is properly positioned on the dual-lumen catheter 340, the physician inserts the proximal end 351 of the guidewire 350 into the distal end of the inner lumen 342 in the dual-lumen catheter 340. The dual-lumen catheter 340 and retractor 300 are advanced over the guidewire 350 and into the patient. As the catheter 340 and retractor 300 are advanced, negative pressure is applied to the outer lumen of the catheter, for example, through use of a syringe 360 attached to the proximal end of the outer lumen 358. Once the indicator hole 352 is advanced to a position inside the artery, blood will be drawn through the indicator hole 352 and will become visible in the outer lumen of the catheter 340 and the syringe 360. At this point, advancement of the catheter 340 and retractor 300 are stopped, as the catheter 340 and retractor 300 are properly positioned in the patient.

Once properly positioned at the site of the puncture wound, the two halves of the retracting portion 308a, 308b are separated slightly, using the handles 316a, 316b at the proximal end 304 of the retractor 300. To separate the retracting portions 308a, 308b, the screw 322 is loosened, and the handles 316a, 316b manipulated into the desired position. The screw 322 is then tightened down upon the loop 320, prohibiting further movement of the handles 316a, 316b, and the corresponding retracting portions 308a, 308b.

At this point, the surrounding tissues have been displaced, forming an access path to the puncture wound, and the puncture wound may be visible. The dual-lumen catheter 340 is removed from the patient by withdrawing it over the guidewire 350. The guidewire 350 is left in place, and the wound closure device, such as a clip applicator, is inserted over the guidewire 350 to the site of the wound. Clips, such as those made of titanium or a biodegradable material, are applied to the wound, as the guidewire 350 is removed. If necessary, the artery is compressed to stop the flow of blood out of the puncture wound during the closing of the wound. The closing device is removed when the physician is confident that the wound is closed, and the retractor 300 is removed from the patient.

Alternatively, a separate inner catheter 360 is used in the system of present invention. In this embodiment, once the retractor 300 and dual-lumen catheter 340 are in place, and the retracting portion 308 is in an open position, the dual-lumen catheter 340 is left in place, and the guidewire 350 is withdrawn from the patient through the inner lumen 342. An inner catheter 360 having an inflatable balloon 362 at its distal end is inserted through the inner lumen 342 and into the patient. Once the distal balloon 362 is advanced past the distal tip 346 of the dual-lumen catheter 340, the balloon 362 is inflated. The dual-lumen catheter 340 is removed from the patient, leaving the inner catheter 360 in place.

To properly position the balloon inside the patient's artery, the physician can measure the distance from the distal tip of the dual-lumen catheter 346 to just outside the patient's body when the catheter 340 is properly positioned. The physician then inserts the inner catheter 360 just slightly more than that distance, to ensure that the distal balloon 362 is within the artery. The physician then pulls the inner catheter 360 in a proximal direction until resistance is felt. This will place the balloon 362 at the site of the puncture would. The balloon 362 is properly positioned just inside the artery of the patient. The balloon 362 helps to stop the flow of blood out of the puncture wound. The inner catheter 360 is used as a guide for the clip applicator or other closing device used to close the wound. The closing device is advanced until it contacts the inflated balloon 362. As the wound is closed, the balloon 362 is slowly deflated, and the inner catheter 360 is removed from the patient. Finally, once the physician is confident that the wound is closed, the retractor 300 is removed from the patient.

The present invention can also be used with surgical staples or sutures. After the retractor is inserted into the patient's body and positioned at the puncture site as described above, the two halves of the retractor are separated, laterally displacing the tissues surrounding the puncture site. The retractor acts much like a dilator, gradually increasing the displacement of the overlying tissues, until the puncture wound is visible to the physician. The wound can then be closed using any acceptable means for wound closure, including surgical staples and sutures.

Although certain embodiments and examples have been used to illustrate and describe the present invention, it is intended that the scope of the invention not be limited to the specific embodiments set forth herein. The scope of the invention is to be defined by the claims which follow.

What is claimed is:

1. A device to facilitate the closure of wounds in the vasculature of a patient, comprising:
   a body portion having a retracting portion having two elongate movable halves extending away from and substantially perpendicular to said body portion, said halves forming a channel extending completely through said retracting portion, each half having a first end and a second end, the first end being positioned farther from the body portion than the second end, the halves being movable between a retracted position and an approximated position; and
   a handle portion connected to said body portion which controls the movement of the two movable halves, the handle having a grasp portion and a locking mechanism, the grasp portion having two handles, the locking mechanism selectively engagable so as to prevent movement of the halves from the retracted position toward the approximated position, the locking mechanism comprising a loop extending from one handle which surrounds a screw mounted on the other handle.

2. A device to facilitate the closure of wounds in the vasculature of a patient, comprising:
   a body portion having a retracting portion having two elongate movable halves extending away from and substantially perpendicular to said body portion, said halves forming a channel extending completely through said retracting portion, each half having a first end and a second end, the first end being positioned farther from the body portion than the second end, the halves being movable between a retracted position and an approximated position;
   a handle portion connected to said body portion which controls the movement of the two movable halves, the handle having a grasp portion and a locking mechanism, the locking mechanism selectively engagable so as to prevent movement of the halves from the retracted position toward the approximated position; and
   a dual-lumen catheter, having an inner lumen having a proximal end and a distal end, the inner lumen adapted to receive a guidewire therethrough, and an outer lumen having a proximal end and a distal end, the outer lumen surrounding the inner lumen, and the catheter can be inserted through said channel in said retracting portion of said retractor.

3. The device of claim 2, wherein said outer lumen further comprises at least one indicator hole located in an outer wall of said outer lumen.

4. The device of claim 3, further comprising a source of negative pressure in fluid communication with said proximal end of said outer lumen.

5. A method for facilitating the closure of a wound in the vasculature of a patient, comprising the steps of:
   inserting a guidewire having a proximal end and a distal end into said vasculature through said wound, until said distal end of said guidewire is within the vasculature and the proximal end remains outside the patient;
   mounting a retractor comprising a body portion having a retracting portion having two movable halves extending away from and substantially perpendicular to said body portion, said halves forming a channel extending completely through said retracting portion; on a distal end of a dual-lumen catheter having an inner lumen and an outer lumen each having a proximal end and a distal end, wherein said outer lumen surrounds the inner lumen, and having at least one indicator hole located in an outer wall of said outer lumen near the distal end of said outer lumen;
   inserting the proximal end of the guidewire into the distal end of the inner lumen of the dual-lumen catheter;
   advancing said catheter and retractor over the guidewire until the indicator hole enters said wound;
   separating the two halves of the retracting portion; and
   closing said wound.

6. The method of claim 5, wherein said advancing the catheter step further comprises providing a source of negative pressure at the proximal end of said outer lumen, and wherein said advancing step is stopped when blood is drawn into the outer lumen.

7. The method of claim 5, further comprising the steps of:
   removing said guidewire from the patient through said inner lumen following said separating step;
   inserting an inner catheter having an inflatable balloon mounted on its distal end through said inner lumen and into said patient; and
   inflating said balloon prior to said closing step.

8. The method of claim 5, wherein prior to said closing step, the catheter is removed from the patient and a clip applicator is inserted over the guidewire and advanced to the wound.

9. The method of claim 5, wherein said closing step comprises applying at least one clip to the wound using said clip applicator.

10. A device to facilitate the closure of wounds in the vasculature of a patient, comprising:
    a body portion having a retracting portion having two elongate movable halves extending away from and substantially perpendicular to said body portion, said halves forming a channel extending completely through said retracting portion, each half having a first end and a second end, the first end being positioned farther from the body portion than the second end, the halves being movable between a retracted position and an approximated position;
    a handle portion connected to said body portion which controls the movement of the two movable halves, the handle having a grasp portion and a locking mechanism, the locking mechanism selectively engagable so as to prevent movement of the halves from the retracted position toward the approximated position;
    a hollow catheter having an open proximal end and an open distal end, adapted to receive a guidewire therethrough, and said hollow catheter can be inserted through said channel in said retracting portion of said retractor; and a clip applicator adapted to receive a guidewire.

11. A system for facilitating the closure of wounds in the vasculature of a patient, comprising:
   a retractor comprising a body portion having a retracting portion having two movable halves extending away and substantially perpendicular to from said body portion, said halves forming a channel extending completely through said retracting portion; and a handle portion connected to said body portion which controls the movement of the two moveable halves;
   a hollow catheter having an open proximal end and an open distal end, adapted to receive a guidewire therethrough, wherein said hollow catheter can be inserted through said channel in said retracting portion of said retractor; and
   a clip applicator adapted to receive said guidewire.

12. A surgical apparatus, which comprises a retractor and a catheter, the retractor including an elongated body portion having proximal and distal ends and defining a longitudinal axis and a handle connected to the body portion and obliquely arranged relative to the longitudinal axis, the distal end of the body portion being positioned farther from the handle than is the proximal end of the body portion, the elongated body portion including at least two separate cooperating members, each cooperating member having internal surfaces dimensioned to define a longitudinal passage extending through the elongated body portion for reception of surgical instrumentation, the cooperating members operatively connected to each other and adapted for relative movement between an approximated position wherein the internal surfaces of the cooperating members engage the surgical instrumentation and a displaced position wherein the surgical instrumentation is movable relative to the cooperating members, the handle including first and second movable members connected about a pin to define a scissors-grip configuration, the first and second movable members operatively connected to respective first and second cooperating members of the body portion to cause relative movement thereof between the approximated and displaced positions, and a locking mechanism operatively connected to the first and second movable members of the handle, the locking mechanism adapted to selectively lock the first and second movable members at desired relative positions to thereby secure the cooperating members of the body portion at corresponding desired relative positions between the approximated and displaced positions, the catheter having a catheter shaft defining proximal and distal ends, and being positionable within the longitudinal passageway of the body portion of the retractor, the catheter including an indicator lumen terminating in an indicator port to permit passage of the body fluids to indicate entry within desired tissue.

13. The surgical apparatus according to claim 12 wherein the body portion defines a distal tapered portion for facilitating entry into tissue.

14. The surgical apparatus according to claim 12 wherein the catheter includes a stop region defining an enlarged cross-sectional dimension relative to a region of the catheter shaft proximal of the stop region, the stop region dimensioned to engage the body portion to prevent advancement of the retractor within the tissue.

15. The surgical apparatus according to claim 14 wherein the catheter shaft includes an aperture in a side wall portion of the step region, the aperture being the indicator port.

16. The surgical apparatus according to claim 14, wherein the catheter shaft further includes a guide lumen dimensioned for reception of a guide element.

17. The surgical apparatus according to claim 16 further including a guide element having a guide shaft defining proximal and distal ends, and an inflatable member adjacent the distal end thereof, the guide element positionable within the guide lumen to introduce the inflatable member into the target site.

18. A method for facilitating closure of an opening in a blood vessel where access to the opening is through a tissue passage extending through tissue overlying the blood vessel, comprising the steps of:
   introducing a catheter within the tissue passage and at least partially within the blood vessel, the catheter having a catheter shaft defining proximal and distal ends and an enlarged stop region adjacent the distal end;
   positioning a retractor about the catheter shaft of the catheter, the retractor including an elongated body having proximal and distal ends and defining a longitudinal axis and a handle connected to the elongated body and arranged in oblique relation to the longitudinal axis, the elongated body having first and second body portions defining a longitudinal passage therebetween and being adapted for selective relative movement between an approximated position and a displaced position to accommodate an outer dimension of a wound closure device, the retractor being positioned such that the distal end of the elongated body is adjacent the stop region of the catheter;
   selectively moving at least the first body portion of the retractor relative to the second body portion by manipulating the handle to a predetermined relative position to enlarge the tissue passage;
   removing the catheter from the tissue passage and the retractor; and
   inserting a wound closure device through the first and second body portions of the retractor, and actuating the wound closure device to close the opening in the blood vessel.

19. The method according to claim 18 wherein the catheter includes an inflatable member disposed adjacent the distal end of the catheter shaft, and wherein the step of introducing includes positioning the inflatable member through the opening and within the blood vessel and further including the step of expanding the inflatable member such that the inflatable member at least partially closes the opening in the blood vessel to minimize flow of blood through the opening.

20. The method according to claim 18 wherein the step of positioning is performed prior to the step of introducing.

21. The method according to claim 18 wherein the catheter includes an indicator lumen terminating in an indicator port in the stop region of the catheter shaft and wherein the step of introducing includes advancing the catheter within the tissue passage whereby the indicator port is disposed within the blood vessel as evidenced by the presence of blood within the indicator lumen.

22. A surgical apparatus comprising a retractor and a catheter, the retractor including an elongated body portion having proximal and distal ends and defining a longitudinal axis and a handle connected to the body portion and obliquely arranged relative to the longitudinal axis, the distal end of the body portion being positioned farther from the handle than is the proximal end of the body portion, the elongated body portion including at least two separate cooperating members, each cooperating member having internal surfaces dimensioned to define a longitudinal passage extending through the elongated body portion for reception of the catheter, the cooperating members operatively connected to each other and adapted for relative movement between an approximated position wherein the internal surfaces of the cooperating members engage the catheter and a displaced position wherein the catheter is movable relative to the cooperating members, the handle including first and second movable members operatively connected to respective first and second cooperating members of the body portion to cause relative movement thereof between the approximated and displaced positions, the catheter having a catheter shaft defining proximal and distal ends, and being positionable within the longitudinal passageway of the body portion of the retractor, the catheter including an indicator lumen configured to permit viewing of body fluids passing through said lumen so as to indicate entry within desired tissue.

23. The surgical apparatus of claim 22, additionally comprising a locking mechanism operatively connected to the first and second movable members of the handle, the locking mechanism adapted to selectively lock the first and second movable members at desired relative positions to thereby secure the cooperating members of the body portion at corresponding desired relative positions between the approximated and displaced positions.

24. The surgical apparatus of claim 23, wherein the catheter has a hole formed through a side of the catheter near a distal end thereof, the hole communicating with the indicator lumen.

25. The surgical apparatus of claim 23, wherein the catheter has a distal opening at a distal end of the catheter, and the distal opening is configured to slidingly accept a guidewire extending therethrough.

26. A device to facilitate the closure of wounds in the vasculature of a patient, comprising:

a body portion having a retracting portion having two elongate movable members extending away from said body portion, said movable members forming a channel through said retracting portion, each movable member having a first end and a second end, the first end being positioned farther from the body portion than the second end, the movable members being movable between a retracted position and an approximated position;

a handle portion connected to said body portion and configured to control the movement of the two movable members, the handle having a grasp portion and a locking mechanism, the locking mechanism selectively engagable so as to prevent movement of the movable members from the retracted position toward the approximated position; and a catheter adapted to be positionable within the channel, the catheter having an open distal end configured to slidingly receive a guidewire therethrough, the catheter further comprising an indicator lumen configured so that a clinician can view fluids drawn through the indicator lumen.

27. The device of claim 26, wherein the catheter has an arcuate outer surface, and the channel has a substantially complementary surface sized and configured to engage the catheter outer surface.

* * * * *